US008067613B2

(12) United States Patent
Gandhi et al.

(10) Patent No.: US 8,067,613 B2
(45) Date of Patent: Nov. 29, 2011

(54) BENZIMIDAZOLE POLY(ADP RIBOSE)POLYMERASE INHIBITORS

(75) Inventors: Virajkumar B. Gandhi, Gurnee, IL (US); Vincent L. Giranda, Gurnee, IL (US); Jianchun Gong, Deerfield, IL (US); Thomas D Penning, Elmhurst, IL (US); Gui-Dong Zhu, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/173,213

(22) Filed: Jul. 15, 2008

(65) Prior Publication Data
US 2009/0030016 A1  Jan. 29, 2009

Related U.S. Application Data

(60) Provisional application No. 60/949,895, filed on Jul. 16, 2007, provisional application No. 60/949,899, filed on Jul. 16, 2007.

(51) Int. Cl.
| | |
|---|---|
| A61K 31/4184 | (2006.01) |
| A61K 31/454 | (2006.01) |
| A61K 31/4439 | (2006.01) |
| C07D 401/04 | (2006.01) |
| C07D 409/04 | (2006.01) |
| C07D 417/14 | (2006.01) |

(52) U.S. Cl. ............... 548/304.7; 548/305.1; 548/306.1; 546/199; 546/273.4; 514/322; 514/338; 514/394

(58) Field of Classification Search ............... 548/306.1, 548/304.7, 305.1
See application file for complete search history.

(56) References Cited

U.S. PATENT DOCUMENTS

| | | | |
|---|---|---|---|
| 3,864,385 | A | 2/1975 | Feit et al. |
| 4,093,726 | A | 6/1978 | Winn et al. |
| 6,372,736 | B1 | 4/2002 | Kemp et al. |
| 6,448,271 | B1 | 9/2002 | Lubisch et al. |
| 6,509,365 | B1 | 1/2003 | Lubisch et al. |
| 6,696,437 | B1 | 2/2004 | Lubisch et al. |
| 6,737,421 | B1 | 5/2004 | Lubsich et al. |
| 7,166,292 | B2 | 1/2007 | Isele et al. |
| RE39,608 | E | 5/2007 | Lubisch et |
| 7,462,724 | B2 | 12/2008 | Penning et al. |
| 7,550,603 | B2 | 6/2009 | Zhu et al. |
| 2003/0100582 | A1 | 5/2003 | Sircar et al. |
| 2005/0159427 | A1 | 7/2005 | Bruncko et al. |
| 2006/0229289 | A1 | 10/2006 | Zhu et al. |
| 2006/0229351 | A1 | 10/2006 | Zhu et al. |
| 2007/0179136 | A1 | 8/2007 | Penning et al. |
| 2007/0259937 | A1 | 11/2007 | Giranda et al. |
| 2007/0265324 | A1 | 11/2007 | Wernet et al. |

FOREIGN PATENT DOCUMENTS

| | | |
|---|---|---|
| DE | 3522230 | 1/1987 |
| DE | 3830060 A1 | 3/1990 |
| DE | 19916460 A1 | 10/2000 |
| DE | 10021468 A1 | 11/2001 |
| DE | 19920936 A1 | 11/2001 |
| GB | 1354554 A | 6/1974 |
| JP | 2002-141067 A | 5/2002 |
| WO | 97/04771 A1 | 2/1997 |
| WO | 98/39343 A1 | 9/1998 |
| WO | 00/29384 A1 | 5/2000 |
| WO | 00/32579 A1 | 6/2000 |
| WO | 00/26192 A1 | 11/2000 |
| WO | 01/21615 A1 | 3/2001 |
| WO | 01/21634 A1 | 3/2001 |
| WO | 01/82877 A2 | 11/2001 |
| WO | 02/068407 A1 | 9/2002 |
| WO | 03/002698 | 1/2003 |
| WO | 03/094861 A2 | 11/2003 |
| WO | 03/106430 A1 | 12/2003 |
| WO | 2004/054515 A2 | 7/2004 |
| WO | 2004/065370 A1 | 8/2004 |
| WO | 2004/096793 A1 | 11/2004 |
| WO | 2004/098494 A2 | 11/2004 |
| WO | 2007/059230 A2 | 5/2007 |

OTHER PUBLICATIONS

Amundson, et al., "An Informatics Approach Identifying Markers of Chemosensitivity in Human Cancer Cell Lines", Cancer Res, 60(21), 6101-6110 (2000).
Burkart, et al., "Mice lacking the poly(ADP-ribose)polymerase gene are resistant to pancreatic beta-cell destruction and diabetes development induced by streptozocin", Nature Medicine, 5(3), 314-319 (1999).
Chen, et al., "Potentiation of the antitumor activity of cisplation in mice by 3-aminobenzamide and nicotinamide", Cancer Chemotherapy and Pharmacology, 22,303-307 (1988).
Cuzzocrea, et al., "Protective effects of 3-Aminobenzamide, an inhibitor of poly(ADP-ribose) synthase in a carrrageenan-induced model of local inflammation", Eur J Pharmacol, 342, 67-76 (1998).
Ehrlich, et al., "Inhibition of the induction of collagenase by interleukin-1b in cultured rabbit synovial fibroblasts after treatment with the poly(ADP-ribose)-polymerase inhibitoro 3-aminobenzamide", Rheumatol Int, 15, 171-172 (1995).
Holzelova, et al., "Autoimmune Lymphoproliferative Syndrome with Somatic Fas Mutations", N Engl J Med, 31(14), 1409-1418 (2004).
IUPAC 1974 Recommendations for Sec E, Fundamental Stereochemistry, Pure Appl Chem,45,13-30 (1976).
Kroger et al, "Synergistic effects of thalidomide and poly(ADP-ribose) polumerase inhibition on type II collagen-induced arthritis in mice", Inflammation, 20, 203-215 (1996).
Puck,et al., "Immune Disorders Caused by Defects in the Caspase Cascade", Current Allergy and Asthma Reports, 3, 378-384 (2003).
Rengan, et al., "Actin cytoskeletal function is spared, but apoptosis is increased, in WAS patient Hematopoietic cells", Blood, 95(4), 1283-1292 (2000).
Shimazaki, et al., "Evaluation of apoptosis as a prognostic factor in Myelodysplastic syndromes", British Journal of Haematology, 110(3), 584-590 (2000).
Szabo, et al., Protection against peroxynitrite-induced fibroblast injury and arthritis development by inhibition of pyly (ADP-ribose) synthase, Proc Natl Acad Sci USA, 95(7), 3867-3872 (1998).

(Continued)

*Primary Examiner* — Laura L. Stockton
(74) *Attorney, Agent, or Firm* — Susan L. Steele; Rachel A. Polster

(57) ABSTRACT

Compounds which inhibit the activity of poly(ADP-ribose) polymerase (PARP), compositions containing the compounds and methods of treating diseases using them are disclosed.

10 Claims, No Drawings

OTHER PUBLICATIONS

Thiemermann, et al., "Inhibition of the activity of poly(ADP ribose) synthetase reduces ischemia-reperfusion injury in the heart and skeletal muscle", PNAS, 94, 679-683 (1997).
Weltin, et al., "Immunosuppressive activities of 6(5H)-phenanthridinone a new poly(ADP-ribose)Polymerase inhibitor", Int J Immunopharmacol, 17(4), 265-271 (1995).
Co-Pending U.S. Appl. No. 09/830,992, filed May 2001.
Co-Pending U.S. Appl. No. 10/935,683, filed Sep. 2004.
Co-Pending U.S. Appl. No. 11/401,635, filed Apr. 2006.
Co-Pending U.S. Appl. No. 11/536,994, filed Sep. 2006.
Co-Pending U.S. Appl. No. 11/560,166, filed Nov. 2006.
Co-Pending U.S. Appl. No. 11/743,200, filed May 2007.
Search Report No. 20030374, Jun. 13, 2003.
Search Report No. 20030487, Sep. 19, 2003.
Search Report No. 20050150, Apr. 22, 2005.
Search Report No. 20050207, May 27, 2005.
Alexy, et al., "Inhibition of ADP-Evoked Platelet Aggregation by Selected Poly(ADP-Ribose) Polymerase Inhibitors", Journal Cardiovascular Pharmacol 43(3), 423-431 (2004).
Gilchrist, et al., "Cyclisation of ortho-Substituted N-Arylbenzimidoyl Nitrenes. Part 2. Preferential Cyclisations at an ortho-Position Bearin a Methoxycarbonyl Group", Journal of Chem. Society, Perkin Transactions 1, GB, Chemical Society, Letchworth, 2303-2307 (1979).
Griffin, et al., "Resistance modifying agents 3. Novel benzimidazole and quinazolinone inhibitors of the DNA repair enzyme poly(ADP-ribose)polymerase." Pharmaceutical Sciences, 2(1), 43-47 (1996).
Kröger, H., et al., "Synergistic Effects of Thalidomide and Poly(ADP-Ribose) Polymerase Inhibition of Type II Collagen-Induced Arthritis in Mice", Inflammation, 20(2):203-215 (1996).
White, et al., "Potentiation of cytotoxic drug activity in human tumore cell lines, by amine-substituted 2-arylbenzimidazol-4carboxamide PARP-1 inhibitors", Bioorganic & Medicinal Chemistry Letters, 14(10), 2433-2437 (2004).
Co-pending U.S. Appl. No. 11/623,996, filed Jan. 2007.
Co-pending U.S. Appl. No. 11/830,318, filed Jul. 2007.
Co-pending U.S. Appl. No. 11/970,828, filed Jan. 2008.
Co-pending U.S. Appl. No. 12/058,478, filed Mar. 2008.
Co-pending U.S. Appl. No. 12/116,823, filed May 2008.
Co-pending U.S. Appl. No. 12/117,452, filed May 2008.
Co-pending U.S. Appl. No. 12/413,834, filed Mar. 2009.

BENZIMIDAZOLE POLY(ADP RIBOSE)POLYMERASE INHIBITORS

This application claims priority to U.S. Provisional Patent Application Ser. No. 60/949,895 filed Jul. 16, 2007 and U.S. Provisional Patent Application Ser. No. 60/949,899 filed Jul. 16, 2007.

FIELD OF THE INVENTION

This invention comprises compounds which inhibit the activity of poly(ADP-ribose)polymerase (PARP), compositions containing the compounds and methods of treating diseases using them.

BACKGROUND OF THE INVENTION

Poly(ADP-ribose)polymerase (PARP) has an essential role in facilitating DNA repair, controlling RNA transcription, mediating cell death and regulating immune response. PARP inhibitors have demonstrated efficacy in disease models for allergic encephalitis, arthritis, cardiac and kidney toxicities from doxorubicin-based and platinum-based antineoplastic agents, carcinoma of the breast, central nervous system inflammation, cervical carcinoma, colon cancer, diabetes and complications therefrom, glioblastoma, gout, hemmorhagic shock, hypoglycemia, inflammatory bowel disease, ischemia reperfusion injury associated with myocardial infarction, kidney disease, leukemia, liver toxicity following acetominophen overdose, lymphoma, melanoma, multiple sclerosis, myocardial infarction, neural trauma, organ transplantation, Parkinsons disease, potentiation of cytotoxic cancer therapy, pulmonary fibrosis, reperfusion of the eye, gut, kidney and skeletal muscle, retroviral infection, rheumatoid arthritis, sepsis, septic shock, skin damage secondary to sulfur mustards, stroke and other neural trauma and uveitis.

In cancer models, PARP inhibitors have been shown to potentiate radiation and chemotherapy by increasing apoptosis of cancer cells, limiting tumor growth, decreasing metastasis, and prolonging the survival of tumor-bearing animals. There is therefore an existing need in the therapeutic arts for PARP inhibitors.

SUMMARY OF THE INVENTION

The present invention has numerous embodiments. One embodiment this invention, therefore, comprises compounds that are PARP inhibitors, the compounds having Formula I

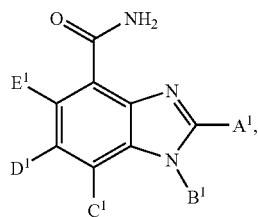

and therapeutically acceptable salts, prodrugs, esters, amides, salts of prodrugs, salts of esters, and salts of amides thereof, wherein $A^1$ is heteroaryl which is substituted with $A^2$ and unfused or fused with benzene, heteroarene or $R^{1A}$; $R^{1A}$ is cycloalkane, cycloalkene, heterocycloalkane or heterocycloalkene;

$A^2$ is heteroaryl, heterocycloalkyl, or heterocycloalkenyl, each of which is unfused or fused with benzene, heteroarene or $R^{2A}$; $R^{2A}$ is cycloalkane, cycloalkene, heterocycloalkane or heterocycloalkene;

$B^1$ is hydrogen, $R^3$, $CO(O)R^{3A}$, $C(O)NH_2$, $C(O)NHR^{3A}$, $C(O)N(R^{3A})_2$, $SO_2NH_2$, $SO_2NHR^{3A}$ or $SO_2N(R^{3A})_2$;

$R^{3A}$ is alkyl or cycloalkyl;

$R^3$ is alkyl or alkenyl each of which is unsubstituted or substituted with one or two of independently selected $R^4$, $OR^4$, $NH_2$, $NHR^4$, $N(R^4)_2$, $C(O)NH_2$, $C(O)NHR^4$, $C(O)N(R^4)_2$ or OH;

$R^4$ is alkyl or cycloalkyl;

$C^1$, $D^1$, $E^1$ are each independently hydrogen, $NO_2$, $CN$, $R^5$, $OR^5$, $CO(O)R^5$, $C(O)NH_2$, $C(O)NHR^5$, $C(O)N(R^5)_2$, $NH_2$, $NHR^5$, $N(R^5)_2$, OH, F, Cl, Br or I;

$R^5$ is alkyl, alkenyl or alkynyl; each of which is unsubstituted or substituted with one or two of independently selected $R^6$, $NH_2$, $NHR^6$, $N(R^6)_2$, $C(O)NH_2$, $C(O)NHR^6$, $C(O)N(R^6)_2$, OH, F, Cl, Br or I;

$R^6$ is alkyl or cycloalkyl;

wherein each foregoing cyclic moiety is independently unsubstituted, further unsubstituted, substituted or further substituted with one or two or three or four or five of independently selected $R^7$, $OR^7$, $SR^7$, $S(O)R^7$, $SO_2R^7$, $C(O)R^7$, $CO(O)R^7$, $OC(O)R^7$, $OC(O)OR^7$, $NO_2$, $NH_2$, $NHR^7$, $N(R^7)_2$, $CH_2R^7$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $CF_3$, $CF_2CF_3$, $C(O)H$, $C(O)OH$, $C(N)NH_2$, $C(N)NHR^7$, $C(N)N(R^7)_2$, CNOH, CNOCH$_3$, OH, (O), $N_3$, $CF_3$, $CF_2CF_3$, $OCF_3$, $OCF_2CF_3$, F, Cl, Br or I;

$R^7$ is $R^8$, $R^9$, $R^{10}$ or $R^{11}$;

$R^8$ is phenyl each of which is unfused or fused with benzene, heteroarene or $R^{8A}$; $R^{8A}$ is cycloalkane, cycloalkene, heterocycloalkane or heterocycloalkene;

$R^9$ is heteroaryl which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl, or alkenyl, each of which is unsubstituted or substituted with one, two, three, four or five of independently selected $R^{12}$, $OR^{12}$, $SR^{12}$, $S(O)R^{12}$, $SO_2R^{12}$, $NH_2$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NR^{12}SO_2R^{12}$, $NHC(O)OR^{12}$, $NR^{12}C(O)OR^{12}$, $SO_2NH_2$, $SO_2NHR^{12}$, $SO_2N(R^{12})_2$, $NHC(O)NH_2$, $NHC(O)R^{12}NHC(O)N(R^{12})_2$, $NR^{12}C(O)N(R^{12})_2$, OH, (O), $C(O)OH$, CN, $CF_3$, $OCF_3$, $CF_2CF_3$, F, Cl, Br or I;

$R^{12}$ is $R^{13}$, $R^{14}$, $R^{15}$ or $R^{16}$;

$R^{13}$ is phenyl which is unfused or fused with benzene, heteroarene or $R^{13A}$; $R^{13A}$ is cycloalkane, cycloalkene, heterocycloalkane or heterocycloalkene;

$R^{14}$ is heteroaryl which is unfused or fused with benzene, heteroarene or $R^{14A}$; $R^{14A}$ is cycloalkane, cycloalkene, heterocycloalkane or heterocycloalkene;

$R^{15}$ is cycloalkyl, cycloalkenyl, heterocycloalkyl or heterocycloalkenyl, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkenyl, each of which is unsubstituted or substituted with $R^{17}$; and $R^{17}$ is phenyl, heteroaryl, cycloalkyl, cycloalkenyl or heterocycloalkyl.

Another embodiment pertains to a compound selected from the group consisting of
2-(4-pyridin-3-yl-1,3-thiazol-2-yl)-1H-benzimidazole-4-carboxamide,
2-(4-pyridin-4-yl-1,3-thiazol-2-yl)-1H-benzimidazole-4-carboxamide,
2-(4-methyl-2-pyrazin-2-yl-1,3-thiazol-5-yl)-1H-benzimidazole-4-carboxamide,
2-(2-thien-2-yl-1,3-thiazol-4-yl)-1H-benzimidazole-4-carboxamide,
2-(2-piperidin-4-yl-1,3-thiazol-4-yl)-1H-benzimidazole-4-carboxamide,
2-(2-(1-methylpiperidin-4-yl)-1,3-thiazol-4-yl)-1H-benzimidazole-4-carboxamide,
2-(2-(1-isopropylpiperidin-4-yl)-1,3-thiazol-4-yl)-1H-benzimidazole-4-carboxamide,
2-(2-(1-propylpiperidin-4-yl)-1,3-thiazol-4-yl)-1H-benzimidazole-4-carboxamide,
2-(2-(1-cyclobutylpiperidin-4-yl)-1,3-thiazol-4-yl)-1H-benzimidazole-4-carboxamide,
2-(5-pyridin-2-ylthien-2-yl)-1H-benzimidazole-4-carboxamide,
2-(5-pyrazin-2-ylthien-2-yl)-1H-benzimidazole-4-carboxamide,
2-(5-pyrimidin-2-ylthien-2-yl)-1H-benzimidazole-4-carboxamide,
2-(5-pyridin-3-ylthien-2-yl)-1H-benzimidazole-4-carboxamide,
2-(5-pyridin-4-ylthien-2-yl)-1H-benzimidazole-4-carboxamide,
2-(5-(1H-pyrrol-2-yl)thien-2-yl)-1H-benzimidazole-4-carboxamide,
2-(5-((2R)-pyrrolidin-2-yl)thien-2-yl)-1H-benzimidazole-4-carboxamide,
2-(5-((2R)-1-methylpyrrolidin-2-yl)thien-2-yl)-1H-benzimidazole-4-carboxamide,
2-(5-((2R)-1-isopropylpyrrolidin-2-yl)thien-2-yl)-1H-benzimidazole-4-carboxamide,
2-(5-((2R)-1-propylpyrrolidin-2-yl)thien-2-yl)-1H-benzimidazole-4-carboxamide,
2-(5-((2R)-1-(cyclopropylmethyl)pyrrolidin-2-yl)thien-2-yl)-1H-benzimidazole-4-carboxamide,
2-(5-((2R)-1-cyclobutylpyrrolidin-2-yl)thien-2-yl)-1H-benzimidazole-4-carboxamide,
2-(5-((2R)-1-cyclopentylpyrrolidin-2-yl)thien-2-yl)-1H-benzimidazole-4-carboxamide,
2-(5-((2R)-1-cyclohexylpyrrolidin-2-yl)thien-2-yl)-1H-benzimidazole-4-carboxamide,
2-(5-((2R)-1-tetrahydro-2H-pyran-4-ylpyrrolidin-2-yl)thien-2-yl)-1H-benzimidazole-4-carboxamide,
2-(5-((2R)-1-(pyridin-2-ylmethyl)pyrrolidin-2-yl)thien-2-yl)-1H-benzimidazole-4-carboxamide,
2-(5-((2R)-1-(pyridin-4-ylmethyl)pyrrolidin-2-yl)thien-2-yl)-1H-benzimidazole-4-carboxamide,
2-(5-((2R)-1-isobutylpyrrolidin-2-yl)thien-2-yl)-1H-benzimidazole-4-carboxamide,
2-(5-piperidin-2-ylthien-2-yl)-1H-benzimidazole-4-carboxamide,
2-(5-(1-methylpiperidin-2-yl)thien-2-yl)-1H-benzimidazole-4-carboxamide,
2-(5-(1-propylpiperidin-2-yl)thien-2-yl)-1H-benzimidazole-4-carboxamide,
2-(5-(1-(cyclopropylmethyl)piperidin-2-yl)thien-2-yl)-1H-benzimidazole-4-carboxamide,
2-(5-(1-cyclobutylpiperidin-2-yl)thien-2-yl)-1H-benzimidazole-4-carboxamide,
2-(5-(1-isobutylpiperidin-2-yl)thien-2-yl)-1H-benzimidazole-4-carboxamide,
2-(5-pyrrolidin-2-ylthien-2-yl)-1H-benzimidazole-4-carboxamide,
2-(5-(1-methylpyrrolidin-2-yl)thien-2-yl)-1H-benzimidazole-4-carboxamide,
2-(5-(1-isopropylpyrrolidin-2-yl)thien-2-yl)-1H-benzimidazole-4-carboxamide,
2-(5-(1-propylpyrrolidin-2-yl)thien-2-yl)-1H-benzimidazole-4-carboxamide,
2-(5-(1-(cyclopropylmethyl)pyrrolidin-2-yl)thien-2-yl)-1H-benzimidazole-4-carboxamide,
2-(5-(1-isobutylpyrrolidin-2-yl)thien-2-yl)-1H-benzimidazole-4-carboxamide,
2-(5-(1-cyclobutylpyrrolidin-2-yl)thien-2-yl)-1H-benzimidazole-4-carboxamide,
2-(5-(1-cyclopentylpyrrolidin-2-yl)thien-2-yl)-1H-benzimidazole-4-carboxamide,
2-(5-(1-cyclohexylpyrrolidin-2-yl)thien-2-yl)-1H-benzimidazole-4-carboxamide,
2-(6-pyrrolidin-2-ylpyridin-3-yl)-1H-benzimidazole-4-carboxamide;
2-[6-(1-isopropylpyrrolidin-2-yl)pyridin-3-yl]-1H-benzimidazole-4-carboxamide;
2-[6-(1-isobutylpyrrolidin-2-yl)pyridin-3-yl]-1H-benzimidazole-4-carboxamide;
2-[6-(1-cyclobutylpyrrolidin-2-yl)pyridin-3-yl]-1H-benzimidazole-4-carboxamide;
2-[6-(1-cyclopentylpyrrolidin-2-yl)pyridin-3-yl]-1H-benzimidazole-4-carboxamide;
2-[6-(1-cyclohexylpyrrolidin-2-yl)pyridin-3-yl]-1H-benzimidazole-4-carboxamide;
2-[6-(1-tetrahydro-2H-pyran-4-ylpyrrolidin-2-yl)pyridin-3-yl]-1H-benzimidazole-4-carboxamide;
2-[6-(1,3-oxazol-5-yl)pyridin-3-yl]-1H-benzimidazole-4-carboxamide;
2-[5-(1,3,4-oxadiazol-2-yl)pyridin-2-yl]-1H-benzimidazole-4-carboxamide;
2-{5-[5-(trifluoromethyl)-1,3,4-oxadiazol-2-yl]pyridin-2-yl}-1H-benzimidazole-4-carboxamide;
2-[5-(5-methyl-1,3,4-oxadiazol-2-yl)pyridin-2-yl]-1H-benzimidazole-4-carboxamide;
and therapeutically acceptable salts, prodrugs, esters, amides, salts of prodrugs, salts of esters, and salts of amides thereof.

Still another embodiment comprises compositions comprising a therapeutically acceptable amount of compound having Formula I, or a salt, prodrug or salt of a prodrug thereof, and an excipient.

Still another embodiment comprises methods of inhibiting poly(ADP-ribose)polymerase in a mammal comprising administering thereto a therapeutically acceptable amount of a compound having Formula I, or a salt, prodrug or salt of a prodrug thereof.

Still another embodiment comprises methods of treating cancer in a mammal comprising administering thereto a therapeutically acceptable amount of a compound having Formula I, $$\text{(I)}$$

or a salt, prodrug or salt of a prodrug thereof, wherein $A^1$ is heteroaryl which is substituted with $A^2$ and unfused or fused with benzene, heteroarene or $R^{1,A}$; $R^{1,A}$ is cycloalkane, cycloalkene, heterocycloalkane or heterocycloalkene;

$A^2$ is heteroaryl, heterocycloalkyl, or heterocycloalkenyl, each of which is unfused or fused with benzene, heteroarene or $R^{2,A}$; $R^{2,A}$ is cycloalkane, cycloalkene, heterocycloalkane or heterocycloalkene;

$B^1$ is hydrogen, $R^3$, $CO(O)R^{3,A}$, $C(O)NH_2$, $C(O)NHR^{3,A}$, $C(O)N(R^{3,A})_2$, $SO_2NH_2$, $SO_2NHR^{3,A}$ or $SO_2N(R^{3,A})_2$;

$R^{3,A}$ is alkyl or cycloalkyl;

$R^3$ is alkyl or alkenyl each of which is unsubstituted or substituted with one or two of independently selected $R^4$, $OR^4$, $NH_2$, $NHR^4$, $N(R^4)_2$, $C(O)NH_2$, $C(O)NHR^4$, $C(O)N(R^4)_2$ or OH;

$R^4$ is alkyl or cycloalkyl;

$C^1$, $D^1$, $E^1$ are each independently hydrogen, $NO_2$, CN, $R^5$, $OR^5$, $CO(O)R^5$, $C(O)NH_2$, $C(O)NHR^5$, $C(O)N(R^5)_2$, $NH_2$, $NHR^5$, $N(R^5)_2$, OH, F, Cl, Br or I;

$R^5$ is alkyl, alkenyl or alkynyl; each of which is unsubstituted or substituted with one or two of independently selected $R^6$, $NH_2$, $NHR^6$, $N(R^6)_2$, $C(O)NH_2$, $C(O)NHR^6$, $C(O)N(R^6)_2$, OH, F, Cl, Br or I;

$R^6$ is alkyl or cycloalkyl;

wherein each foregoing cyclic moiety is independently unsubstituted, further unsubstituted, substituted or further substituted with one or two or three or four or five of independently selected $R^7$, $OR^7$, $SR^7$, $S(O)R^7$, $SO_2R^7$, $C(O)R^7$, $CO(O)R^7$, $OC(O)R^7$, $OC(O)OR^7$, $NO_2$, $NH_2$, $NHR^7$, $N(R^7)_2$, $CH_2R^7$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $CF_3$, $CF_2CF_3$, $C(O)H$, $C(O)OH$, $C(N)NH_2$, $C(N)NHR^7$, $C(N)N(R^7)_2$, CNOH, $CNOCH_3$, OH, (O), $N_3$, $CF_3$, $CF_2CF_3$, $OCF_3$, $OCF_2CF_3$, F, Cl, Br or I;

$R^7$ is $R^8$, $R^9$, $R^{10}$ or $R^{11}$;

$R^8$ is phenyl each of which is unfused or fused with benzene, heteroarene or $R^{8,A}$; $R^{8,A}$ is cycloalkane, cycloalkene, heterocycloalkane or heterocycloalkene;

$R^9$ is heteroaryl which is unfused or fused with benzene, heteroarene or $R^{9,A}$; $R^{9,A}$ is cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene or $R^{10,A}$; $R^{10,A}$ is cycloalkane, cycloalkene, heterocycloalkane or heterocycloalkene;

$R^{11}$ is alkyl, alkenyl, or alkenyl, each of which is unsubstituted or substituted with one, two, three, four or five of independently selected $R^{12}$, $OR^{12}$, $SR^{12}$, $S(O)R^{12}$, $SO_2R^{12}$, $NH_2$, $NHR^{12}$, $N(R^{12})_2$, $C(O)R^{12}$, $C(O)NH_2$, $C(O)N(R^{12})_2$, $NHC(O)R^{12}$, $NR^{12}C(O)R^{12}$, $NHSO_2R^{12}$, $NR^{12}SO_2R^{12}$, $NHC(O)OR^{12}NR^{12}C(O)OR^{12}$, $SO_2NH_2$, $SO_2NHR^{12}$, $SO_2N(R^{12})_2$, $NHC(O)NH_2$, $NHC(O)R^{12}NHC(O)N(R^{12})_2$, $NR^{12}C(O)N(R^{12})_2$, OH, (O), C(O)OH, CN, $CF_3$, $OCF_3$, $CF_2CF_3$, F, Cl, Br or I;

$R^{12}$ is $R^{13}$, $R^{14}$, $R^{15}$ or $R^{16}$;

$R^{13}$ is phenyl which is unfused or fused with benzene, heteroarene or $R^{13,A}$; $R^{13,A}$ is cycloalkane, cycloalkene, heterocycloalkane or heterocycloalkene;

$R^{14}$ is heteroaryl which is unfused or fused with benzene, heteroarene or $R^{14,A}$; $R^{14,A}$ is cycloalkane, cycloalkene, heterocycloalkane or heterocycloalkene;

$R^{15}$ is cycloalkyl, cycloalkenyl, heterocycloalkyl or heterocycloalkenyl, each of which is unfused or fused with benzene, heteroarene or $R^{15,A}$; $R^{15,A}$ is cycloalkane, cycloalkene, heterocycloalkane or heterocycloalkene;

$R^{16}$ is alkyl, alkenyl or alkenyl, each of which is unsubstituted or substituted with $R^{17}$; and $R^{17}$ is phenyl, heteroaryl, cycloalkyl, cycloalkenyl or heterocycloalkyl.

Still another embodiment comprises methods of treating allergic encephalitis, arthritis, cardiac and kidney toxicities from doxorubicin-based and platinum-based antineoplastic agents, carcinoma of the breast, central nervous system inflammation, cervical carcinoma, colon cancer, diabetes and complications therefrom, glioblastoma, gout, hemmorhagic shock, hypoglycemia, inflammatory bowel disease, ischemia reperfusion injury associated with myocardial infarction, kidney disease, leukemia, liver toxicity following acetominophen overdose, lymphoma, melanoma, multiple sclerosis, myocardial infarction, neural trauma, organ transplantation, Parkinsons disease, potentiation of cytotoxic cancer therapy, pulmonary fibrosis, reperfusion of the eye, gut, kidney and skeletal muscle, retroviral infection, rheumatoid arthritis, sepsis, septic shock, skin damage secondary to sulfur mustards, stroke and other neural trama and uveitis in a mammal comprising administering thereto a therapeutically acceptable amount of a compound having Formula I $$\text{(I)}$$

or a salt, prodrug or salt of a prodrug thereof, wherein $A^1$ is heteroaryl which is substituted with $A^2$ and unfused or fused with benzene, heteroarene or $R^{1,A}$; $R^{1,A}$ is cycloalkane, cycloalkene, heterocycloalkane or heterocycloalkene;

$A^2$ is heteroaryl, heterocycloalkyl, or heterocycloalkenyl, each of which is unfused or fused with benzene, heteroarene or $R^{2,A}$; $R^{2,A}$ is cycloalkane, cycloalkene, heterocycloalkane or heterocycloalkene;

$B^1$ is hydrogen, $R^3$, $CO(O)R^{3,A}$, $C(O)NH_2$, $C(O)NHR^{3,A}$, $C(O)N(R^{3,A})_2$, $SO_2NH_2$, $SO_2NHR^{3,A}$ or $SO_2N(R^{3,A})_2$;

$R^{3,A}$ is alkyl or cycloalkyl;

$R^3$ is alkyl or alkenyl each of which is unsubstituted or substituted with one or two of independently selected $R^4$, $OR^4$, $NH_2$, $NHR^4$, $N(R^4)_2$, $C(O)NH_2$, $C(O)NHR^4$, $C(O)N(R^4)_2$ or OH;

$R^4$ is alkyl or cycloalkyl;

$C^1$, $D^1$, $E^1$ are each independently hydrogen, $NO_2$, CN, $R^5$, $OR^5$, $CO(O)R^5$, $C(O)NH_2$, $C(O)NHR^5$, $C(O)N(R^5)_2$, $NH_2$, $NHR^5$, $N(R^5)_2$, OH, F, Cl, Br or I;

$R^5$ is alkyl, alkenyl or alkynyl; each of which is unsubstituted or substituted with one or two of independently selected $R^6$, $NH_2$, $NHR^6$, $N(R^6)_2$, $C(O)NH_2$, $C(O)NHR^6$, $C(O)N(R^6)_2$, OH, F, Cl, Br or I;

$R^6$ is alkyl or cycloalkyl;

wherein each foregoing cyclic moiety is independently unsubstituted, further unsubstituted, substituted or further substituted with one or two or three or four or five of independently selected $R^7$, $OR^7$, $SR^7$, $S(O)R^7$, $SO_2R^7$, $C(O)R^7$, $CO(O)R^7$, $OC(O)R^7$, $OC(O)OR^7$, $NO_2$, $NH_2$, $NHR^7$, $N(R^7)_2$, $CH_2R^7$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $CF_3$, $CF_2CF_3$, $C(O)H$, $C(O)OH$, $C(N)NH_2$, $C(N)NHR^7$, $C(N)N(R^7)_2$, CNOH, $CNOCH_3$, OH, (O), $N_3$, $CF_3$, $CF_2CF_3$, $OCF_3$, $OCF_2CF_3$, F, Cl, Br or I;

$R^7$ is $R^8$, $R^9$, $R^{10}$ or $R^{11}$;

$R^8$ is phenyl each of which is unfused or fused with benzene, heteroarene or $R^{8A}$; $R^{8A}$ is cycloalkane, cycloalkene, heterocycloalkane or heterocycloalkene;

$R^9$ is heteroaryl which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl, or alkenyl, each of which is unsubstituted or substituted with one, two, three, four or five of independently selected $R^{12}$, $OR^{12}$, $SR^{12}$, $S(O)R^{12}$, $SO_2R^{12}$, $NH_2$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NR^{12}SO_2R^{12}$, $NHC(O)OR^{12}$, $NR^{12}C(O)OR^{12}$, $SO_2NH_2$, $SO_2NHR^{12}$, $SO_2N(R^{12})_2$, $NHC(O)NH_2$, $NHC(O)R^{12}NHC(O)N(R^{12})_2$, $NR^{12}C(O)N(R^{12})_2$, OH, (O), C(O)OH, CN, $CF_3$, $OCF_3$, $CF_2CF_3$, F, Cl, Br or I;

$R^{12}$ is $R^{13}$, $R^{14}$, $R^{15}$ or $R^{16}$;

$R^{13}$ is phenyl which is unfused or fused with benzene, heteroarene or $R^{13A}$; $R^{13A}$ is cycloalkane, cycloalkene, heterocycloalkane or heterocycloalkene;

$R^{14}$ is heteroaryl which is unfused or fused with benzene, heteroarene or $R^{14A}$; $R^{14A}$ is cycloalkane, cycloalkene, heterocycloalkane or heterocycloalkene;

$R^{15}$ is cycloalkyl, cycloalkenyl, heterocycloalkyl or heterocycloalkenyl, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkenyl, each of which is unsubstituted or substituted with $R^{17}$; and $R^{17}$ is phenyl, heteroaryl, cycloalkyl, cycloalkenyl or heterocycloalkyl.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Variable moieties of compounds herein are represented by identifiers (capital letters with numerical and/or alphabetical superscripts) and may be specifically embodied.

It is meant to be understood that proper valences are maintained for all combinations herein, that monovalent moieties having more than one atom are attached through their left ends, and that divalent moieties are drawn from left to right.

It is also meant to be understood that a specific embodiment of a variable moiety may be the same or different as another specific embodiment having the same identifier.

The term "alkenyl," as used herein, means monovalent, straight or branched chain hydrocarbon moieties having one or more than one carbon-carbon double bonds, such as $C_2$-alkenyl, $C_3$-alkenyl, $C_4$-alkenyl, $C_5$-alkenyl, $C_6$-alkenyl and the like.

The term "alkenylene," as used herein, means divalent, straight or branched chain hydrocarbon moieties having one or more than one carbon-carbon double bonds, such as $C_2$-alkenylene, $C_3$-alkenylene, $C_4$-alkenylene, $C_5$-alkenylene, $C_6$-alkenylene and the like.

The term "alkyl," as used herein, means monovalent, saturated, straight or branched chain hydrocarbon moieties, such as $C_1$-alkyl, $C_2$-alkyl, $C_3$-alkyl, $C_4$-alkyl, $C_5$-alkyl, $C_6$-alkyl and the like.

The term "alkylene," as used herein, means divalent, saturated, straight or branched chain hydrocarbon moieties, such as $C_1$-alkylene, $C_2$-alkylene, $C_3$-alkylene, $C_4$-alkylene, $C_5$-alkylene, $C_6$-alkylene and the like.

The term "alkynyl," as used herein, means monovalent, straight or branched chain hydrocarbon moieties having one or more than one carbon-carbon triple bonds, such as $C_2$-alkynyl, $C_3$-alkynyl, $C_4$-alkynyl, $C_5$-alkynyl, $C_6$-alkynyl and the like.

The term "alkynylene," as used herein, means divalent, straight or branched chain hydrocarbon moieties having one or more than one carbon-carbon triple bonds, such as $C_2$-alkynylene, $C_3$-alkynylene, $C_4$-alkynylene, $C_5$-alkynylene, $C_6$-alkynylene and the like.

The term "cycloalkane," as used herein, means saturated cyclic or bicyclic hydrocarbon moieties, such as $C_4$-cycloalkane, $C_5$-cycloalkane, $C_6$-cycloalkane, $C_7$-cycloalkane, $C_8$-cycloalkane, $C_9$-cycloalkane, $C_{10}$-cycloalkane, $C_{11}$-cycloalkane, $C_{12}$-cycloalkane and the like.

The term "cycloalkyl," as used herein, means monovalent, saturated cyclic and bicyclic hydrocarbon moieties, such as $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl and the like.

The term "cycloalkene," as used herein, means cyclic and bicyclic hydrocarbon moieties having one or more than one carbon-carbon double bonds, such as $C_5$-cycloalkene, $C_6$-cycloalkene, $C_7$-cycloalkene, $C_8$-cycloalkene, $C_9$-cycloalkene, $C_{10}$-cycloalkene, $C_{11}$-cycloalkene, $C_{12}$-cycloalkene and the like.

The term "cycloalkenyl," as used herein, means monovalent, cyclic hydrocarbon moieties having one or more than one carbon-carbon double bonds, such as $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, $C_{11}$-cycloalkenyl, $C_{12}$-cycloalkenyl and the like.

The term "heteroarene," as used herein, means furan, imidazole, isothiazole, isoxazole, 1,2,3-oxadiazole, 1,2,5-oxadiazole, 1,3,4-oxadiazole, oxazole, pyrazine, pyrazole, pyridazine, pyridine, pyrimidine, pyrrole, thiazole, 1,3,4-thiadiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, 1,3,4-oxadiazolyl, oxazolyl, pyrazinyl, pyrazolyl, pyridazinyl, pyridinyl, pyrimidinyl, pyrrolyl, tetrazolyl, thiazolyl, 1,2,3-thiadiazoyl, 1,2,5-thiadiazolyl, 1,3,4-thiadiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), $SO_2$ or NH and one or two CH moieties replaced with N.

The term "heterocycloalkyl," as used herein, means cycloalkyl having one or two or three $CH_2$ moieties replaced with independently selected O, S, S(O), $SO_2$ or NH and one or two CH moieties unreplaced or replaced with N and also means cycloalkyl having one or two or three $CH_2$ moieties unreplaced or replaced with independently selected O, S, S(O), $SO_2$ or NH and one or two CH moieties replaced with N.

The term "heterocycloalkenyl," as used herein, means cycloalkenyl having one or two or three $CH_2$ moieties replaced with independently selected O, S, S(O), $SO_2$ or NH and one or two CH moieties unreplaced or replaced with N and also means cycloalkenyl having one or two or three $CH_2$ moieties unreplaced or replaced with independently selected O, S, S(O), $SO_2$ or NH and one or two CH moieties replaced with N.

The term "perhaloalkenyl," as used herein, means alkenyl wherein each of the hydrogens thereof are replaced by independently selected F, Cl or Br.

The term "perhaloalkyl," as used herein, means alkyl wherein each of the hydrogens thereof are replaced by independently selected F, Cl or Br.

The term "perhaloalkynyl," as used herein, means alkynyl wherein each of the hydrogens thereof are replaced by independently selected F, Cl or Br.

The term "spiroalkenyl," as used herein, means divalent hydrocarbon moieties having both ends attached to the same carbon atom and having one or more than one carbon-carbon double bonds, such as $C_3$-spiroalkenyl, $C_4$-spiroalkenyl, $C_5$-spiroalkenyl and the like.

The term "spiroalkyl," as used herein, means saturated, divalent hydrocarbon moieties having both ends attached to the same carbon atom, such as $C_2$-spiroalkyl, $C_3$-spiroalkyl, four $C_4$-spiroalkyl, $C_5$-spiroalkyl and the like.

The term "spiroheteroalkenyl," as used herein, means spiroalkenyl having one or two $CH_2$ moieties replaced with independently selected O, S, S(O), $SO_2$ or NH and one or two CH moieties unreplaced or replaced with N and also means spiroalkenyl having one or two $CH_2$ moieties unreplaced or replaced with independently selected O, S, S(O), $SO_2$ or NH and one or two CH moieties replaced with N.

The term "spiroheteroalkyl," as used herein, means spiroalkyl having one or two $CH_2$ moieties replaced with independently selected O, S, S(O), $SO_2$ or NH and one or two CH moieties unreplaced or replaced with N and also means spiroalkyl having one or two $CH_2$ moieties unreplaced or replaced with independently selected O, S, S(O), $SO_2$ or NH and one or two CH moieties replaced with N.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl and phenyl, spiroalkyl, spiroalkenyl, spiroheteroalkyl and spiroheteroalkenyl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures, relative and absolute diastereoisomers and the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention containing NH, C(O)H, C(O)OH, C(O)$NH_2$, OH or SH moieties may have attached thereto prodrug-forming moieties. The prodrug-forming moieties are removed by metabolic processes and release the compounds having the freed NH, C(O)H, C(O)OH, C(O)$NH_2$, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I, produced by in vitro or in vivo metabolic processes, may also have utility for treating diseases associated with overexpressed or unregulated poly(ADP-ribose)polymerase.

Certain precursor compounds of compounds having Formula I may be metabolized in vitro or in vivo to form compounds having Formula I and may thereby also have utility for treating diseases caused or exacerbated by overexpressed or unregulated poly(ADP-ribose)polymerase.

Compounds having Formula I may also be radiolabeled with a radioactive isotope such as a radioactive isotope of carbon (i.e. $^{13}C$), hydrogen (i.e. $^3H$), nitrogen (i.e. $^{15}N$), phosphorus (i.e. $^{32}P$), sulfur (i.e. $^{35}S$) or iodide (i.e. $^{125}I$). Radioactive isotopes may be incorporated into the compounds having Formula I by reacting the same and a radioactive derivitizing agent or by incorporating a radiolabeled intermediate into their syntheses. The radiolabeled compounds of Formula I are useful for both prognostic and diagnostic applications as well as for in vivo and in vitro imaging.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide, or phosphate of cations such as lithium, sodium, potassium, calcium and magnesium.

Compounds having Formula I may be administered, for example, bucally, ophthalmically, orally, osmotically, parenterally (intramuscularly, intraperintoneally intrasternally, intravenously, subcutaneously), rectally, topically, transdermally and vaginally.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.001 to about 200 mg/kg body weight. Single dose compositions contain these amounts or a combination of submultiples thereof.

Compounds having Formula I may be administered with or without an excipient. Excipients include, for example, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Compounds having Formula I may be radiolabeled with a radioactive isotope such as carbon (i.e. $^{13}C$), hydrogen (i.e. $^3H$), nitrogen (i.e. $^{15}N$), phosphorus (i.e. $^{32}P$), sulfur (i.e. $^{35}S$), iodide (i.e. $^{125}I$) and the like. Radioactive isotopes may be incorporated into the compounds having Formula I by reacting the same and a radioactive derivitizing agent or by incorporating a radiolabeled intermediate into their syntheses. The radiolabeled compounds of Formula I are useful for both prognostic and diagnostic applications and for in vivo and in vitro imaging.

Compounds having Formula I may be incorporated into devices such as, but not limited to, arterio-venous grafts, billiary stents, by-pass grafts, catheters, central nervous system shunts, coronary stents, drug delivery balloons, peripheral stents and uretural stents, each of which may be used in areas such as, but not limited to, the vasculature for introduction of a compound having Formula I into selected tissues or organs in the body. One measure of the effectivness of compounds having Formula I is reduction or elimination of device-associated thrombi and complications associated therewith.

Compounds having Formula I can used as a radiosensitizers which enhance the efficacy of radiotherapy. Examples of radiotherapy include, but are not limited to, external beam radiotherapy, teletherapy, brachtherapy and sealed and unsealed source radiotherapy.

Excipients for preparation of compositions comprising a compound having Formula I to be administered orally include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water and mixtures thereof. Excipients for preparation of compositions comprising a compound having Formula I to be administered ophthalmically or orally include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound having Formula I to be administered osmotically include, for example, chlorofluoro-hydrocarbons, ethanol, water and mixtures thereof. Excipients for preparation of compositions comprising a compound having Formula I to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound having Formula I to be administered rectally or vaginally include, for example, cocoa butter, polyethylene glycol, wax and mixtures thereof.

Nicotinamide[2,5',8-3H]adenine dinucleotide and strepavidin SPA beads were obtained from Amersham Biosiences (UK). Recombinant Human Poly(ADP-Ribose)Polymerase (PARP), purified from $E.\ coli$ and 6-Biotin-17-NAD$^+$, were obtained from Trevigen (Gaithersburg, Md.). NAD$^+$, histone, aminobenzamide, 3-aminobenzamide and Calf Thymus DNA (dcDNA) were obtained from Sigma (St. Louis, Mo.). Stem loop oligonucleotide containing MCAT sequence was obtained from Qiagen. The oligos were dissolved to 1 mM in annealing buffer containing 10 mM Tris HCl (pH 7.5), 1 mM EDTA, and 50 mM NaCl, incubated for 5 minutes at 95° C. and annealed at 45° C. for 45 minutes. Histone H1 (95% electrophoretically pure) was obtained from Roche (Indianapolis, Ind. Biotinylated histone H1 was prepared by treating the protein with Sulfo-NHS-LC-Biotin (Pierce Rockford, Ill.). The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 minute then incubation at 4° C. for 1 hour. Streptavidin coated (FlashPlate Plus) microplates were obtained from Perkin Elmer (Boston, Mass.).

PARP1 assay was conducted in PARP assay buffer containing 50 mM tris (pH 8.0), 1 mM DTT and 4 mM MgCl$_2$. PARP reactions contained 1.5 μM [$^3$H]-NAD$^+$ (1.6 μCi/mmol), 200 nM biotinylated histone H1, 200 nM slDNA, and 1 nM PARP enzyme. Auto reactions utilizing SPA bead-based detection were carried out in 100 μL volumes in white 96 well plates.

Reactions were initiated by adding 50 μL of 2×NAD$^+$ substrate mixture to 50 μL of 2× enzyme mixture containing PARP and DNA. These reactions were terminated by the addition of 150 μL of 1.5 mM benzamide (1000-fold over its IC$_{50}$). 170 μL of the stopped reaction mixtures were transferred to streptavidin Flash Plates, incubated for 1 hour and counted using a TopCount microplate scintillation counter. The K$_i$ data (in nM) for representative compounds of this invention were determined from inhibition curves at various substrate concentrations and are shown in TABLE 1.

TABLE 1

| Example | PARP-1 ($K_i$, nM) |
|---|---|
| 1 | 14.5 |
| 2 | 11.8 |
| 3 | 28 |
| 4 | 20.9 |
| 5 | 32 |
| 6 | 45 |
| 7 | 61 |
| 8 | 50 |
| 9 | 44 |
| 10 | 3.1 |
| 11 | 2 |
| 12 | 9 |
| 13 | 2.4 |
| 14 | 3.2 |
| 15 | 5 |
| 16 | 6 |
| 17 | 10 |
| 18 | 6 |
| 19 | 8 |
| 20 | 5 |
| 21 | 4 |
| 22 | 3 |
| 23 | 8 |
| 24 | 12 |
| 25 | 10 |
| 26 | 6 |
| 27 | 8 |
| 28 | 7 |
| 29 | 14 |
| 30 | 16 |
| 31 | 11 |
| 32 | 23 |
| 33 | 21 |
| 34 | 7 |
| 35 | 7 |
| 36 | 5 |
| 37 | 7 |
| 38 | 6 |
| 39 | 11 |
| 40 | 10 |
| 41 | 5 |
| 42 | 12 |
| 43 | 3 |
| 44 | 41 |
| 45 | 11 |
| 46 | 17 |
| 47 | 14 |
| 48 | 14 |
| 49 | 17 |
| 50 | 0.8 |
| 51 | 1.8 |
| 52 | 14 |
| 53 | 317 |

These data demonstrate the utility of representative compounds having Formula I as inhibitors of poly(ADP-ribose) polymerase.

Involvement of PARP in cancer, stroke, ischemia and inflammation is described in Pharm. Res. 52, 2005. Involvement of PARP in other disease states is reported in Cancer Chemo. Pharmacol. 22 (1988), 303; Proc. Natl. Acad. Sci. USA 94 (1997), 679-683 D; Int. J. Immunopharmacol. 17 (1995), 265-271; Inflammation 20 (1996), 203-215; Rheumatol. Int. 15 (1995), 171-172; Proc. Natl. Acad. Sci. USA 95 (1998), 3867-3872; Eur. J. Pharmacol. 342 (1998), 67-76 and Nature Medicine (1999), 5314-19.

Compounds having Formula I are also expected to be useful when used with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immuno-liposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin®(trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FC1, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTITN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having Formula I may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSI-DEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE®LA (lanreotide), SORIATANE® (acitretin), staurosporine (Streptomyces staurospores), talabostat (PT100), TARGRETIN® (bexarotene), Taxoprexin (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

It is also expected that compounds having Formula I would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351(14): 1409-1418).

Compounds having Formula I may be made by synthetic chemical processes, examples of which are shown hereinbelow. It is meant to be understood that the order of the steps in the processes may be varied, that reagents, solvents and reaction conditions may be substituted for those specifically mentioned, and that vulnerable moieties such as C(O)OH, C(O) and C(O)H, NH, C(O)NH$_2$, OH and SH moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like.

Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl (phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

A discussion protecting groups is provided in T. H. Greene and P. G. M. Wuts, Protective Groups in Organic Synthesis, 3rd Ed., John Wiley & Sons, New York (1999).

The following abbreviations have the meanings indicated. ADDP means 1,1'-(azodicarbonyl)dipiperidine; AD-mix-β means a mixture of (DHQD)$_2$ PHAL, K$_3$Fe(CN)$_6$, K$_2$CO$_3$ and K$_2$SO$_4$); 9-BBN means 9-borabicyclo[3.3.1]nonane; CDI means carbonyldiimidazole; (DHQD)$_2$PHAL means hydroquinidine 1,4-phthalazinediyl diethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)butane; dppe means 1,2-bis(diphenylphosphino)ethane; dppf means 1,1'-bis (diphenylphosphino)ferrocene; dppm means 1,1-bis(diphenylphosphino)methane; EDAC means 1-(3-dimethylaminopropyl)-3-ethylcarbodiimide; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; MP-BH$_3$ means macroporus triethylammonium methylpolystyrene cyanoborohydride; PyBOP means benzotriazol-1-yloxytripyrrolidinophosphonium hexafluorophosphate; TEA means triethylamine; TFA means trifluoroacetic acid; THF means tetrahydrofuran; NCS means N-chlorosuccinimide; NMM means N-methylmorpholine; NMP means N-methylpyrrolidine; PPh$_3$ means triphenylphosphine; BOC means Di-tert-butyl dicarbonate; C-18 means dimethyl-octadecylsilane; DCI means chemical ionization for direct introduction; DME means 1,2-dimethoxyethane; ESI means electrospray ionization; HPLC means high performance liquid chromatography; MS means mass spectrometry; as used in reference to $^1$H NMR, the symbol "δ" refers to a $^1$H NMR chemical shift; as used in reference to $^1$H NMR, the abbreviation "br" refers to a broad $^1$H NMR signal; as used in reference to $^1$H NMR, the abbreviation "d" refers to a doublet $^1$H NMR peak; as used in reference to $^1$H NMR, the abbreviation "dd" refers to a doublet of doublets $^1$H NMR peak; as used in reference to $^1$H NMR, the abbreviation "m" refers to a multiplet $^1$H NMR peak; as used in reference to $^1$H NMR, the abbreviation "q" refers to a quartet $^1$H NMR peak; as used in reference to $^1$H NMR, the abbreviation "s" refers to a singlet $^1$H NMR peak; and as used in reference to $^1$H NMR, the abbreviation "t" refers to a triplet $^1$H NMR peak.

Compounds of Formula I

One embodiment comprises compounds of Formula I,

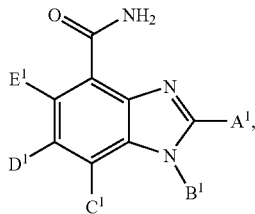

(I)

and therapeutically acceptable salts, prodrugs, esters, amides, salts of prodrugs, salts of esters, and salts of amides thereof, wherein $A^1$ is heteroaryl which is substituted with $A^2$ and unfused or fused with benzene, heteroarene or $R^{1A}$; $R^{1A}$ is cycloalkane, cycloalkene, heterocycloalkane or heterocycloalkene;

$A^2$ is heteroaryl, heterocycloalkyl, or heterocycloalkenyl, each of which is unfused or fused with benzene, heteroarene or $R^{2A}$; $R^{2A}$ is cycloalkane, cycloalkene, heterocycloalkane or heterocycloalkene;

$B^1$ is hydrogen, $R^3$, $CO(O)R^{3A}$, $C(O)NH_2$, $C(O)NHR^{3A}$, $C(O)N(R^{3A})_2$, $SO_2NH_2$, $SO_2NHR^{3A}$ or $SO_2N(R^{3A})_2$;

$R^{3A}$ is alkyl or cycloalkyl;

$R^3$ is alkyl or alkenyl each of which is unsubstituted or substituted with one or two of independently selected $R^4$, $OR^4$, $NH_2$, $NHR^4$, $N(R^4)_2$, $C(O)NH_2$, $C(O)NHR^4$, $C(O)N(R^4)_2$ or OH;

$R^4$ is alkyl or cycloalkyl;

$C^1$, $D^1$, $E^1$ are each independently hydrogen, $NO_2$, CN, $R^5$, $OR^5$, $CO(O)R^5$, $C(O)NH_2$, $C(O)NHR^5$, $C(O)N(R^5)_2$, $NH_2$, $NHR^5$, $N(R^5)_2$, OH, F, Cl, Br or I;

$R^5$ is alkyl, alkenyl or alkynyl; each of which is unsubstituted or substituted with one or two of independently selected $R^6$, $NH_2$, $NHR^6$, $N(R^6)_2$, $C(O)NH_2$, $C(O)NHR^6$, $C(O)N(R^6)_2$, OH, F, Cl, Br or I;

$R^6$ is alkyl or cycloalkyl;

wherein each foregoing cyclic moiety is independently unsubstituted, further unsubstituted, substituted or further substituted with one or two or three or four or five of independently selected $R^7$, $OR^7$, $SR^7$, $S(O)R^7$, $SO_2R^7$, $C(O)R^7$, $CO(O)R^7$, $OC(O)R^7$, $OC(O)OR^7$, $NO_2$, $NH_2$, $NHR^7$, $N(R^7)_2$, $CH_2R^7$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $CF_3$, $CF_2CF_3$, $C(O)H$, $C(O)OH$, $C(N)NH_2$, $C(N)NHR^7$, $C(N)N(R^7)_2$, CNOH, CNOCH$_3$, OH, (O), $N_3$, $CF_3$, $CF_2CF_3$, $OCF_3$, $OCF_2CF_3$, F, Cl, Br or I;

$R^7$ is $R^8$, $R^9$, $R^{10}$ or $R^{11}$;

$R^8$ is phenyl each of which is unfused or fused with benzene, heteroarene or $R^{8A}$; $R^{8A}$ is cycloalkane, cycloalkene, heterocycloalkane or heterocycloalkene;

$R^9$ is heteroaryl which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl, or alkenyl, each of which is unsubstituted or substituted with one, two, three, four or five of independently selected $R^{12}$, $OR^{12}$, $SR^{12}$, $S(O)R^{12}$, $SO_2R^{12}$, $NH_2$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NR^{12}SO_2R^{12}$, $NHC(O)OR^{12}$, $NR^{12}C(O)OR^{12}$, $SO_2NH_2$, $SO_2NHR^{12}$, $SO_2N(R^{12})_2$, $NHC(O)NH_2$, $NHC(O)R^{12}NHC(O)N(R^{12})_2$, $NR^{12}C(O)N(R^{12})_2$, OH, (O), $C(O)OH$, CN, $CF_3$, $OCF_3$, $CF_2CF_3$, F, Cl, Br or I;

$R^{12}$ is $R^{13}$, $R^{14}$, $R^{15}$ or $R^{16}$;

$R^{13}$ is phenyl which is unfused or fused with benzene, heteroarene or $R^{13A}$; $R^{13A}$ is cycloalkane, cycloalkene, heterocycloalkane or heterocycloalkene;

$R^{14}$ is heteroaryl which is unfused or fused with benzene, heteroarene or $R^{14A}$; $R^{14A}$ is cycloalkane, cycloalkene, heterocycloalkane or heterocycloalkene;

$R^{15}$ is cycloalkyl, cycloalkenyl, heterocycloalkyl or heterocycloalkenyl, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkenyl, each of which is unsubstituted or substituted with $R^{17}$; and $R^{17}$ is phenyl, heteroaryl, cycloalkyl, cycloalkenyl or heterocycloalkyl.

Embodiments of Formula I

Selected subclasses of compounds of interest that fall within the scope of the compounds of Formula I are shown in the various embodiments described below, wherein $A^1$, $A^2$, $R^{1A}$, $R^{2A}$, $B^1$, $R^3$, $R^{3A}$, $R^4$, $C^1$, $D^1$, $E^1$, $R^5$, $R^6$, $R^7$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ can be as defined for the compounds of Formula I and as defined in the various embodiments described throughout this specification.

In one embodiment of Formula I, exactly one of $B^1$, $C^1$, $D^1$, and $E^1$ is hydrogen and the remaining are as described in Formula I.

In another embodiment of Formula I, exactly two of $B^1$, $C^1$, $D^1$, and $E^1$ are hydrogen and the remaining are as described in Formula I.

In another embodiment of Formula I, exactly three of $B^1$, $C^1$, $D^1$, and $E^1$ are hydrogen and the remaining are as described in Formula I.

Embodiments of Formula II

In one embodiment, the present invention is directed, in part, to a class of compounds having a structure of Formula II

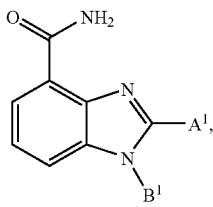

(II)

and therapeutically acceptable salts, prodrugs, esters, amides, salts of prodrugs, salts of esters, and salts of amides thereof, wherein $A^1$ is heteroaryl which is substituted with $A^2$ and unfused or fused with benzene, heteroarene or $R^{1A}$; $R^{1A}$ is cycloalkane, cycloalkene, heterocycloalkane or heterocycloalkene;

$A^2$ is heteroaryl, heterocycloalkyl, or heterocycloalkenyl, each of which is unfused or fused with benzene, heteroarene or $R^{2A}$; $R^{2A}$ is cycloalkane, cycloalkene, heterocycloalkane or heterocycloalkene;

$B^1$ is hydrogen, $R^3$, $CO(O)R^{3A}$, $C(O)NH_2$, $C(O)NHR^{3A}$, $C(O)N(R^{3A})_2$, $SO_2NH_2$, $SO_2NHR^{3A}$ or $SO_2N(R^{3A})_2$;

$R^{3A}$ is alkyl or cycloalkyl;

$R^3$ is alkyl or alkenyl each of which is unsubstituted or substituted with one or two of independently selected $R^4$, $OR^4$, $NH_2$, $NHR^4$, $N(R^4)_2$, $C(O)NH_2$, $C(O)NHR^4$, $C(O)N(R^4)_2$ or $OH$;

$R^4$ is alkyl or cycloalkyl;

wherein each foregoing cyclic moiety is independently unsubstituted, further unsubstituted, substituted or further substituted with one or two or three or four or five of independently selected $R^7$, $OR^7$, $SR^7$, $S(O)R^7$, $SO_2R^7$, $C(O)R^7$, $CO(O)R^7$, $OC(O)R^7$, $OC(O)OR^7$, $NO_2$, $NH_2$, $NHR^7$, $N(R^7)_2$, $CH_2R^7$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $CF_3$, $CF_2CF_3$, $C(O)H$, $C(O)OH$, $C(N)NH_2$, $C(N)NHR^7$, $C(N)N(R^7)_2$, $CNOH$, $CNOCH_3$, $OH$, $(O)$, $N_3$, $CF_3$, $CF_2CF_3$, $OCF_3$, $OCF_2CF_3$, F, Cl, Br or I;

$R^7$ is $R^8$, $R^9$, $R^{10}$ or $R^{11}$;

$R^8$ is phenyl each of which is unfused or fused with benzene, heteroarene or $R^{8A}$; $R^{8A}$ is cycloalkane, cycloalkene, heterocycloalkane or heterocycloalkene;

$R^9$ is heteroaryl which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl, or alkenyl, each of which is unsubstituted or substituted with one, two, three, four or five of independently selected $R^{12}$, $OR^{12}$, $SR^{12}$, $S(O)R^{12}$, $SO_2R^{12}$, $NH_2$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, $NR^{12}SO_2R^{12}$, $NHC(O)OR^{12}$, $NR^{12}C(O)OR^{12}$, $SO_2NH_2$, $SO_2NHR^{12}$, $SO_2N(R^{12})_2$, $NHC(O)NH_2$, $NHC(O)R^{12}NHC(O)N(R^{12})_2$, $NR^{12}C(O)N(R^{12})_2$, $OH$, $(O)$, $C(O)OH$, $CN$, $CF_3$, $OCF_3$, $CF_2CF_3$, F, Cl, Br or I;

$R^{12}$ is $R^{13}$, $R^{14}$, $R^{15}$ or $R^{16}$;

$R^{13}$ is phenyl which is unfused or fused with benzene, heteroarene or $R^{13A}$; $R^{13A}$ is cycloalkane, cycloalkene, heterocycloalkane or heterocycloalkene;

$R^{14}$ is heteroaryl which is unfused or fused with benzene, heteroarene or $R^{14A}$; $R^{14A}$ is cycloalkane, cycloalkene, heterocycloalkane or heterocycloalkene;

$R^{15}$ is cycloalkyl, cycloalkenyl, heterocycloalkyl or heterocycloalkenyl, each of which is unfused or fused with benzene, heteroarene or $R^{15A}$; $R^{15A}$ is cycloalkane, cycloalkene, heterocycloalkane or heterocycloalkene;

$R^{16}$ is alkyl, alkenyl or alkenyl, each of which is unsubstituted or substituted with $R^{17}$; and $R^{17}$ is phenyl, heteroaryl, cycloalkyl, cycloalkenyl or heterocycloalkyl.

In another embodiment of Formula II, $B^1$ is H, as described in Formula III:

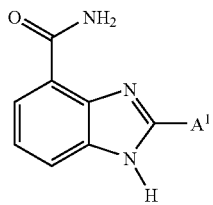

(III)

wherein $A^1$ is heteroaryl which is substituted with $A^2$ and unfused or fused with benzene, heteroarene or $R^{1A}$; $R^{1A}$ is cycloalkane, cycloalkene, heterocycloalkane or heterocycloalkene;

$A^2$ is heteroaryl, heterocycloalkyl, or heterocycloalkenyl, each of which is unfused or fused with benzene, heteroarene or $R^{2A}$; $R^{2A}$ is cycloalkane, cycloalkene, heterocycloalkane or heterocycloalkene;

wherein each foregoing cyclic moiety is independently unsubstituted, further unsubstituted, substituted or further substituted with one or two or three or four or five of independently selected $R^7$, $OR^7$, $SR^7$, $S(O)R^7$, $SO_2R^7$, $C(O)R^7$, $CO(O)R^7$, $OC(O)R^7$, $OC(O)OR^7$, $NO_2$, $NH_2$, $NHR^7$, $N(R^7)_2$, $CH_2R^7$, $C(O)NH_2$, $C(O)NHR^7$, $C(O)N(R^7)_2$, $C(O)NHOH$, $C(O)NHOR^7$, $C(O)NHSO_2R^7$, $C(O)NR^7SO_2R^7$, $SO_2NH_2$, $SO_2NHR^7$, $SO_2N(R^7)_2$, $CF_3$, $CF_2CF_3$, $C(O)H$, $C(O)OH$, $C(N)NH_2$, $C(N)NHR^7$, $C(N)N(R^7)_2$, $CNOH$, $CNOCH_3$, $OH$, $(O)$, $N_3$, $CF_3$, $CF_2CF_3$, $OCF_3$, $OCF_2CF_3$, F, Cl, Br or I;

$R^7$ is $R^8$, $R^9$, $R^{10}$ or $R^{11}$;

$R^8$ is phenyl each of which is unfused or fused with benzene, heteroarene or $R^{8A}$; $R^{8A}$ is cycloalkane, cycloalkene, heterocycloalkane or heterocycloalkene;

$R^9$ is heteroaryl which is unfused or fused with benzene, heteroarene or $R^{9A}$; $R^{9A}$ is cycloalkane, cycloalkene, heterocycloalkane or heterocycloalkene;

$R^{10}$ is cycloalkyl, cycloalkenyl, heterocycloalkyl or heterocycloalkenyl, each of which is unfused or fused with benzene, heteroarene or $R^{10A}$; $R^{10A}$ is cycloalkane, cycloalkene, heterocycloalkane or heterocycloalkene;

$R^{11}$ is alkyl, alkenyl, or alkenyl, each of which is unsubstituted or substituted with one, two, three, four or five of independently selected $R^{12}$, $OR^{12}$, $SR^{12}$, $S(O)R^{12}$, $SO_2R^{12}$, $NH_2$, $NHR^{12}$, $N(R^{12})_2$, $C(O)R^{12}$, $C(O)NH_2$, $C(O)NHR^{12}$, $C(O)N(R^{12})_2$, $NHC(O)R^{12}$, $NR^{12}C(O)R^{12}$, $NHSO_2R^{12}$, NR$^{12}$SO$_2$R$^{12}$, NHC(O)OR$^{12}$, NR$^{12}$C(O)OR$^{12}$, SO$_2$NH$_2$, SO$_2$NHR$^{12}$, SO$_2$N(R$^{12}$)$_2$, NHC(O)NH$_2$, NHC(O)R$^{12}$NHC(O)N(R$^{12}$)$_2$, NR$^{12}$C(O)N(R$^{12}$)$_2$, OH, (O), C(O)OH, CN, CF$_3$, OCF$_3$, CF$_2$CF$_3$, F, Cl, Br or I;

R$^{12}$ is R$^{13}$, R$^{14}$, R$^{15}$ or R$^{16}$;

R$^{13}$ is phenyl which is unfused or fused with benzene, heteroarene or R$^{13A}$; R$^{13A}$ is cycloalkane, cycloalkene, heterocycloalkane or heterocycloalkene;

R$^{14}$ is heteroaryl which is unfused or fused with benzene, heteroarene or R$^{14A}$; R$^{14A}$ is cycloalkane, cycloalkene, heterocycloalkane or heterocycloalkene;

R$^{15}$ is cycloalkyl, cycloalkenyl, heterocycloalkyl or heterocycloalkenyl, each of which is unfused or fused with benzene, heteroarene or R$^{15A}$; R$^{15A}$ is cycloalkane, cycloalkene, heterocycloalkane or heterocycloalkene;

R$^{16}$ is alkyl, alkenyl or alkenyl, each of which is unsubstituted or substituted with R$^{17}$; and R$^{17}$ is phenyl, heteroaryl, cycloalkyl, cycloalkenyl or heterocycloalkyl.

In another embodiment of Formula II, B$^1$ is H, as in Formula III wherein A$^1$ is heteroaryl which is substituted with A$^2$ and unfused or fused with benzene, heteroarene or R$^{1A}$; R$^{1A}$ is cycloalkane, cycloalkene, heterocycloalkane or heterocycloalkene;

A$^2$ is heteroaryl, heterocycloalkyl, or heterocycloalkenyl, each of which is unfused or fused with benzene, heteroarene or R$^{2A}$; R$^{2A}$ is cycloalkane, cycloalkene, heterocycloalkane or heterocycloalkene;

wherein each foregoing cyclic moiety is independently unsubstituted, further unsubstituted, substituted or further substituted with one or two or three or four or five of independently selected R$^7$, CF$_3$, CF$_2$CF$_3$, F, Cl, Br or I;

R$^7$ is R$^8$, R$^9$, R$^{10}$ or R$^{11}$;

R$^8$ is phenyl each of which is unfused or fused with benzene, heteroarene or R$^{8A}$; R$^{8A}$ is cycloalkane, cycloalkene, heterocycloalkane or heterocycloalkene;

R$^9$ is heteroaryl which is unfused or fused with benzene, heteroarene or R$^{9A}$; R$^{9A}$ is cycloalkane, cycloalkene, heterocycloalkane or heterocycloalkene;

R$^{10}$ is cycloalkyl, cycloalkenyl, heterocycloalkyl or heterocycloalkenyl, each of which is unfused or fused with benzene, heteroarene or R$^{10A}$; R$^{10A}$ is cycloalkane, cycloalkene, heterocycloalkane or heterocycloalkene;

R$^{11}$ is alkyl, alkenyl, or alkenyl, each of which is unsubstituted or substituted with one, two, three, four or five of independently selected R$^{12}$, OR$^{12}$, SR$^{12}$, S(O)R$^{12}$, SO$_2$R$^{12}$, NH$_2$, NHR$^{12}$, N(R$^{12}$)$_2$, C(O)R$^{12}$, C(O)NH$_2$, C(O)NHR$^{12}$, C(O)N(R$^{12}$)$_2$, NHC(O)R$^{12}$, NR$^{12}$C(O)R$^{12}$, NHSO$_2$R$^{12}$, NR$^{12}$SO$_2$R$^{12}$, NHC(O)OR$^{12}$, NR$^{12}$C(O)OR$^{12}$, SO$_2$NH$_2$, SO$_2$NHR$^{12}$, SO$_2$N(R$^{12}$)$_2$, NHC(O)NH$_2$, NHC(O)R$^{12}$NHC(O)N(R$^{12}$)$_2$, NR$^{12}$C(O)N(R$^{12}$)$_2$, OH, (O), C(O)OH, CN, CF$_3$, OCF$_3$, CF$_2$CF$_3$, F, Cl, Br or I;

R$^{12}$ is R$^{13}$, R$^{14}$, R$^{15}$ or R$^{16}$;

R$^{13}$ is phenyl which is unfused or fused with benzene, heteroarene or R$^{13A}$; R$^{13A}$ is cycloalkane, cycloalkene, heterocycloalkane or heterocycloalkene;

R$^{14}$ is heteroaryl which is unfused or fused with benzene, heteroarene or R$^{14A}$; R$^{14A}$ is cycloalkane, cycloalkene, heterocycloalkane or heterocycloalkene;

R$^{15}$ is cycloalkyl, cycloalkenyl, heterocycloalkyl or heterocycloalkenyl, each of which is unfused or fused with benzene, heteroarene or R$^{15A}$; R$^{15A}$ is cycloalkane, cycloalkene, heterocycloalkane or heterocycloalkene;

R$^{16}$ is alkyl, alkenyl or alkenyl, each of which is unsubstituted or substituted with R$^{17}$; and R$^{17}$ is phenyl, heteroaryl, cycloalkyl, cycloalkenyl or heterocycloalkyl.

Embodiments of A$^1$ in Formula III

In one embodiment of Formula III, A$^1$ is heteroaryl, which is unfused; and A$^2$, R$^{2A}$, R$^7$, R$^8$, R$^9$, R$^{10}$, R$^{11}$, R$^{8A}$, R$^{9A}$, R$^{10A}$, R$^{12}$, R$^{13}$, R$^{14}$, R$^{15}$, R$^{16}$, R$^{17}$, R$^{13A}$, R$^{14A}$, and R$^{15A}$ are as described in Formula III wherein A$^1$ and A$^2$ are unsubstituted or substituted as described in Formula III.

In another embodiment of Formula III, A$^1$ is heteroaryl, which is unfused; A$^2$ is heteroaryl or heterocycloalkyl, each of which is unfused or fused with R$^{2A}$; and R$^{2A}$, R$^7$, R$^8$, R$^9$, R$^{10}$, R$^{11}$, R$^{8A}$, R$^{9A}$, R$^{10A}$, R$^{12}$, R$^{13}$, R$^{14}$, R$^{15}$, R$^{16}$, R$^{17}$, R$^{13A}$, R$^{14A}$, and R$^{15A}$ are as described in Formula III wherein A$^1$ and A$^2$ are unsubstituted or substituted as described in Formula III.

In another embodiment of Formula III, A$^1$ is heteroaryl, which is unfused; A$^2$ is heteroaryl or heterocycloalkyl, each of which is unfused; and R$^7$, R$^8$, R$^9$, R$^{10}$, R$^{11}$, R$^{8A}$, R$^{9A}$, R$^{10A}$, R$^{12}$, R$^{13}$, R$^{14}$, R$^{15}$, R$^{16}$, R$^{17}$, R$^{13A}$, R$^{14A}$, and R$^{15A}$ are as described in Formula III wherein A$^1$ and A$^2$ are unsubstituted or substituted as described in Formula III.

In another embodiment of Formula III, A$^1$ is heteroaryl, which is unfused; A$^2$ is heteroaryl which is unfused or fused with R$^{2A}$; and R$^{2A}$, R$^7$, R$^8$, R$^9$, R$^{10}$, R$^{11}$, R$^{8A}$, R$^{9A}$, R$^{10A}$, R$^{12}$R$^{13}$, R$^{14}$, R$^{15}$, R$^{16}$, R$^{17}$, R$^{13A}$, R$^{14A}$, and R$^{15A}$ are as described in Formula III wherein A$^1$ and A$^2$ are unsubstituted or substituted as described in Formula III.

In another embodiment of Formula III, A$^1$ is heteroaryl, which is unfused; A$^2$ is heteroaryl which is unfused; and R$^7$, R$^8$, R$^9$, R$^{10}$, R$^{11}$, R$^{8A}$, R$^{9A}$, R$^{10A}$, R$^{12}$, R$^{13}$, R$^{14}$, R$^{15}$, R$^{16}$, R$^{17}$, R$^{13A}$, R$^{14A}$, and R$^{15A}$ are as described in Formula III wherein A$^1$ and A$^2$ are unsubstituted or substituted as described in Formula III.

In another embodiment of Formula III, A$^1$ is heteroaryl, which is unfused; A$^2$ is heterocycloalkyl which is unfused or fused with R$^{2A}$; and R$^{2A}$, R$^7$, R$^8$, R$^9$, R$^{10}$, R$^{11}$, R$^{8A}$, R$^{9A}$ R$^{10A}$, R$^{12}$, R$^{13}$, R$^{14}$, R$^{15}$, R$^{16}$, R$^{17}$, R$^{13A}$, R$^{14A}$, and R$^{15A}$ are as described in Formula III wherein A$^1$ and A$^2$ are unsubstituted or substituted as described in Formula III.

In another embodiment of Formula III, A$^1$ is heteroaryl, which is unfused; A$^2$ is heterocycloalkyl which is unfused; and R$^7$, R$^8$, R$^9$, R$^{10}$, R$^{11}$, R$^{8A}$, R$^{9A}$, R$^{10A}$, R$^{12}$, R$^{13}$, R$^{14}$, R$^{15}$, R$^{16}$, R$^{17}$, R$^{13A}$, R$^{14A}$, and R$^{15A}$ are as described in Formula III wherein A$^1$ and A$^2$ are unsubstituted or substituted as described in Formula III.

In another embodiment of Formula III, A$^1$ is selected from the group consisting of wherein A$^2$, R$^{2A}$, R$^7$, R$^8$, R$^9$, R$^{10}$, R$^{11}$, R$^{8A}$, R$^{9A}$, R$^{10A}$, R$^{12}$R$^{13}$, R$^{14}$, R$^{15}$, R$^{16}$, R$^{17}$, R$^{13A}$, R$^{14A}$, and R$^{15A}$ are as described in Formula III wherein $A^1$ and $A^2$ are unsubstituted or substituted as described in Formula III.

In another embodiment of Formula III, $A^1$ is selected from the group consisting of

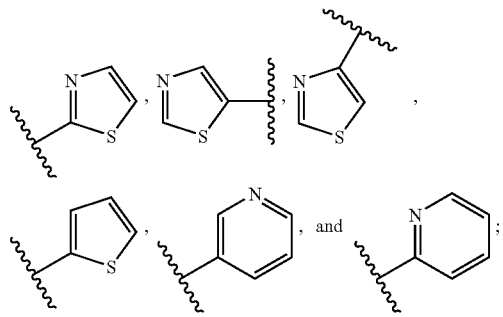

wherein $A^2$ is heteroaryl or heterocycloalkyl, each of which is unfused or fused with $R^{2A}$; and $R^{2A}$, $R^7$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

In another embodiment of Formula III, $A^1$ is selected from the group consisting of

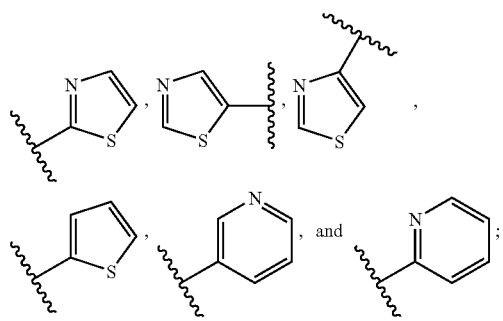

wherein $A^2$ is heteroaryl or heterocycloalkyl, each of which is unfused; and $R^7$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

In another embodiment of Formula III, $A^1$ is selected from the group consisting of

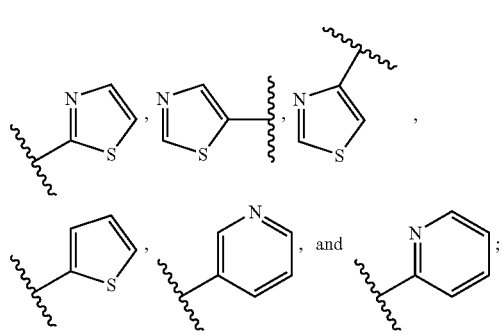

wherein $A^2$ is heteroaryl which is unfused or fused with $R^{2A}$; and $R^{2A}$, $R^7$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

In another embodiment of Formula III, $A^1$ is selected from the group consisting of

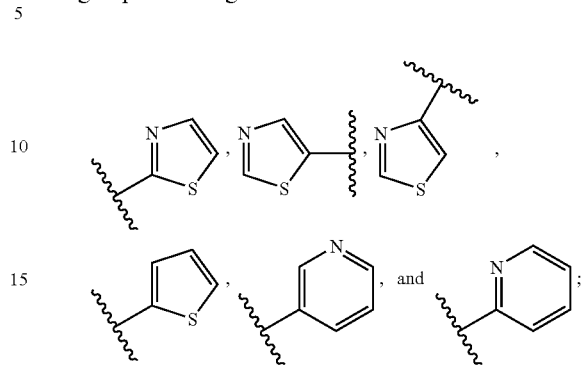

wherein $A^2$ is heteroaryl which is unfused; and $R^7$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

In another embodiment of Formula III, $A^1$ is selected from the group consisting of

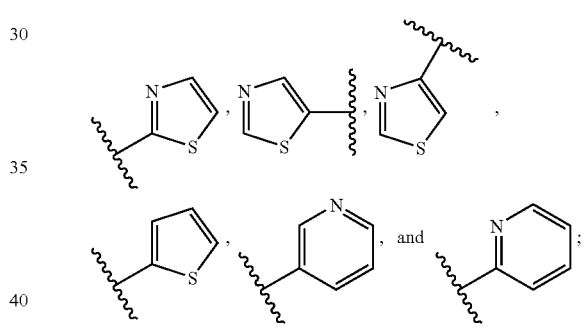

wherein $A^2$ is heterocycloalkyl which is unfused or fused with $R^{2A}$; and $R^{2A}$, $R^7$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

In another embodiment of Formula III, $A^1$ is selected from the group consisting of Sand

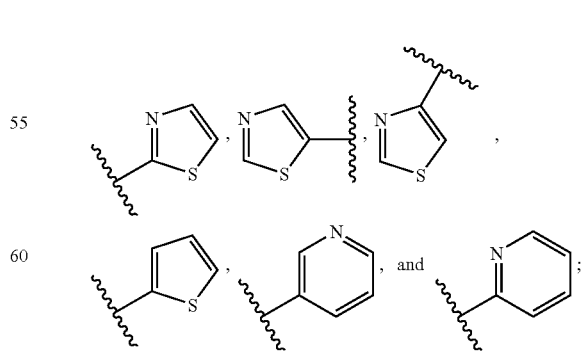

wherein $A^2$ is heterocycloalkyl which is unfused; and $R^7$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

Embodiments of $A^2$ in Formula III

In one embodiment of Formula III, $A^1$ is heteroaryl, which is unfused; $A^2$ is selected from the group consisting of

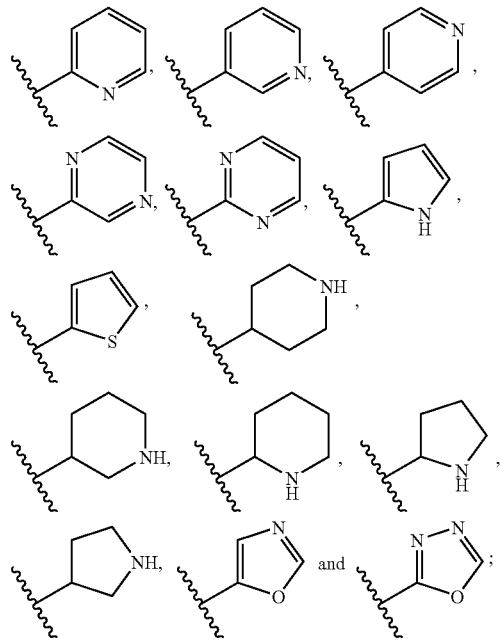

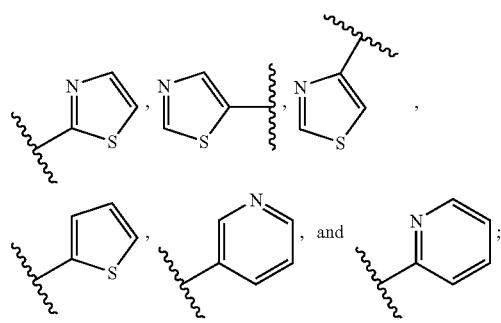

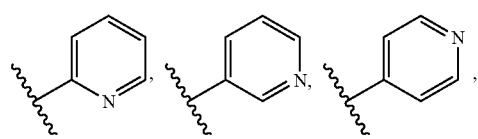

wherein $R^{2A}$, $R^7$, $R^8$, $R^9$, $R^{10}$, $R^{11}$, $R^{8A}$, $R^{9A}$, $R^{10A}$, $R^{12}$, $R^3$, $R^{14}$, $R^5$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

In another embodiment of Formula III, $A^1$ is selected from the group consisting of

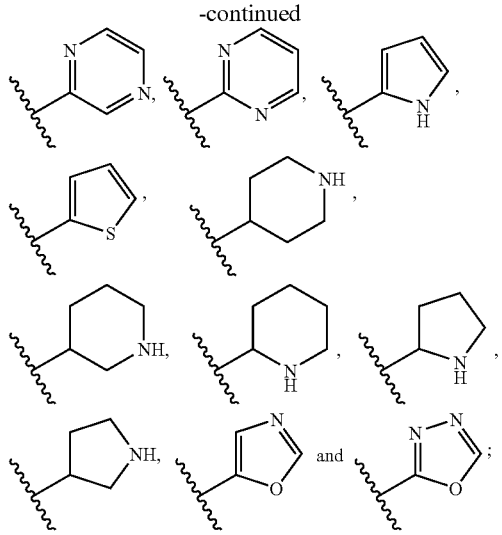

wherein $R^{2A}$, $R^7$, $R^8$, $R^9$, $R^{10}$, $R^{11}$, $R^{8A}$, $R^{9A}$, $R^{10A}$, $R^{12}$, $R^{13}$, $R^{14}$, $R^5$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

In another embodiment of Formula III, $A^1$ is selected from the group consisting of

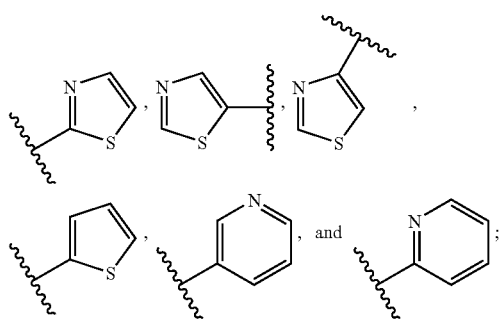

wherein $A^2$ is selected from the group consisting

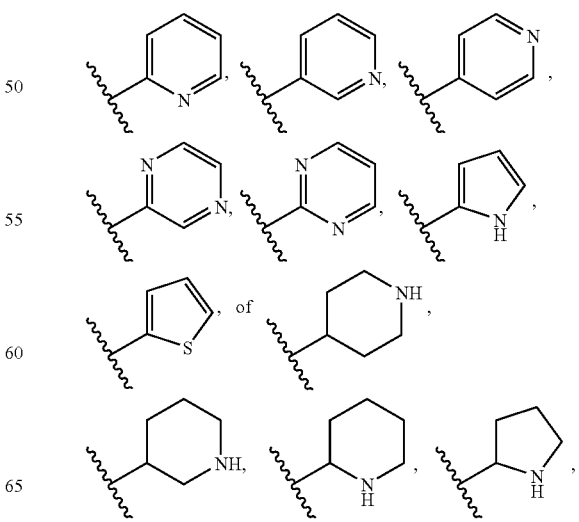

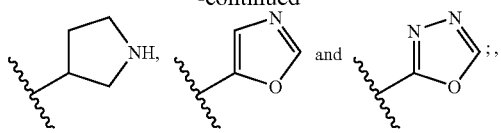 and 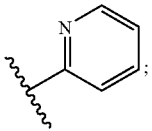;

of which is unfused; and $R^7$, $R^8$, $R^9$, $R^{10}$, $R^{11}$, $R^{8A}$, $R^{9A}$, $R^{1A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted as described in Formula III.

Optional Substituents on Rings

In one embodiment of Formula III, $A^1$ is heteroaryl, which is unfused; $A^2$ is selected from the group consisting of

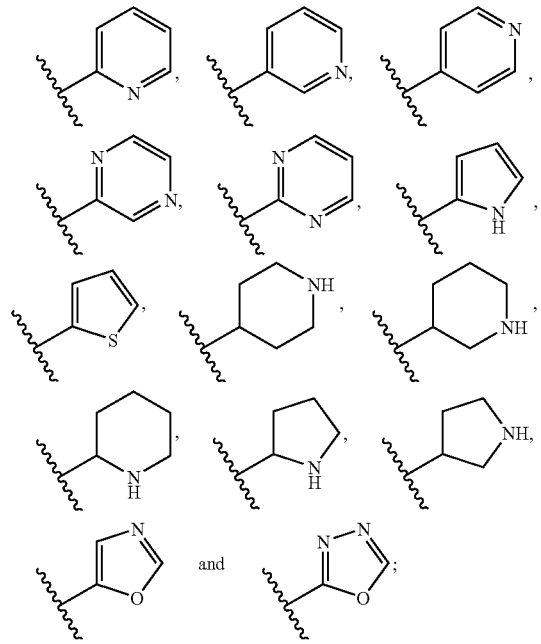

wherein $R^{2A}$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted with $R^7$ or $CF_3$ as described in Formula III.

In another embodiment of Formula III, $A^1$ is selected from the group consisting of

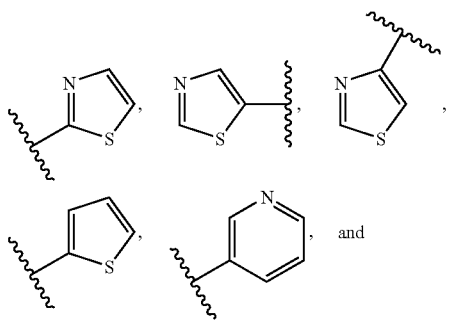

selected from the group consisting of

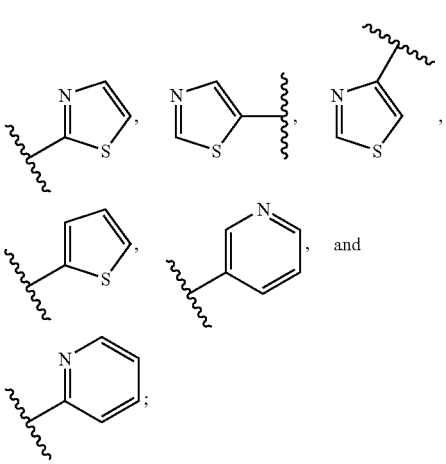

wherein $R^{2A}$, $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted with $R^7$ or $CF_3$ as described in Formula III.

In another embodiment of Formula III, $A^1$ is selected from the group consisting of wherein $A^2$ is selected from the group consisting of

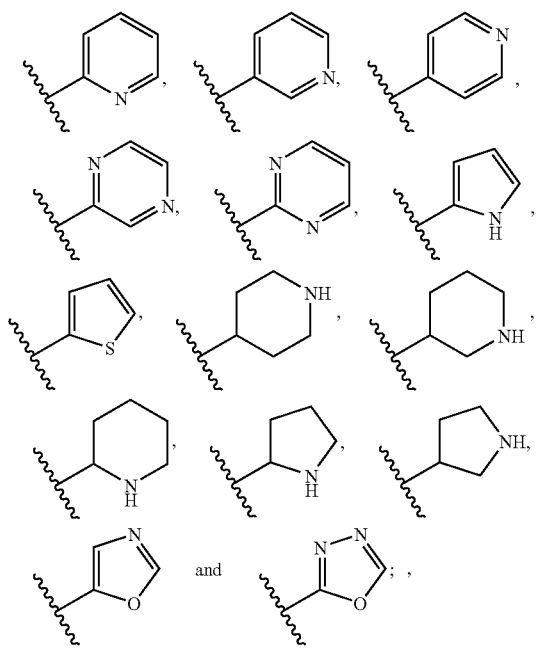

which is unfused; and $R^8$, $R^9$, $R^{10}$, $R^{11}$, $R^{8A}$, $R^{9A}$, $R^{10A}$, $R^{12}$, $R^{13}$, $R^{14}$, $R^{15}$, $R^{16}$, $R^{17}$, $R^{13A}$, $R^{14A}$, and $R^{15A}$ are as described in Formula III wherein $A^1$ and $A^2$ are unsubstituted or substituted with $R^7$ or $CF_3$ as described in Formula III.

In one embodiment of Formula III, $A^1$ is heteroaryl, which is unfused; $A^2$ is selected from the group consisting of

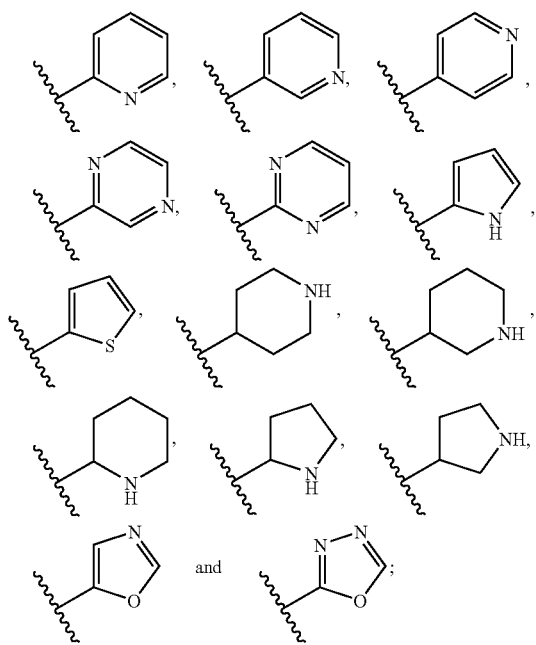

wherein $A^1$ and $A^2$ are unsubstituted or substituted with $R^7$ or $CF_3$ as described in Formula III; each $R^7$ is $R^{10}$ or $R^{11}$; $R^{10}$ is cycloalkyl or heterocycloalkyl; each of which is unfused; each $R^{11}$ is alkyl which is unsubstituted or substituted with $R^{12}$; each $R^{12}$ is $R^{14}$ or $R^{15}$; each of which is unfused; $R^{14}$ is heteroaryl and $R^{15}$ is cycloalkyl each of which are unfused.

In another embodiment of Formula III, $A^1$ is selected from the group consisting of

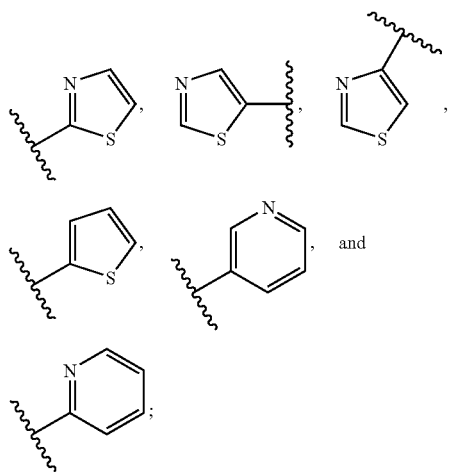

selected from the group consisting of

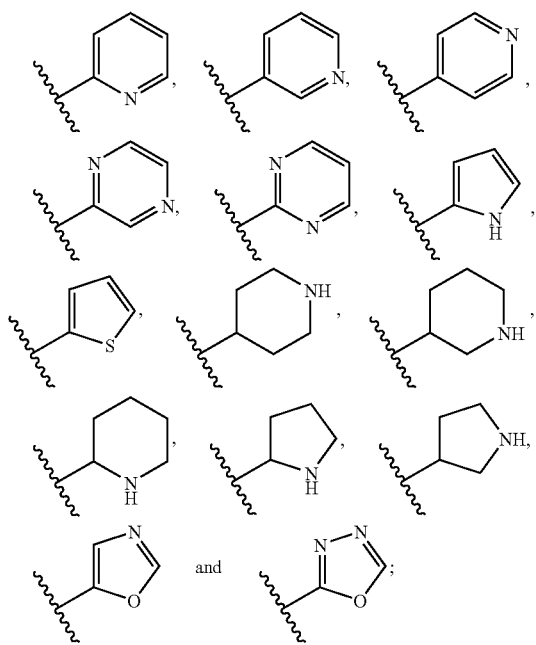

wherein $A^1$ and $A^2$ are unsubstituted or substituted with $R^7$ or $CF_3$ as described in Formula III; each $R^7$ is $R^{10}$ or $R^{11}$; $R^{10}$ is cycloalkyl or heterocycloalkyl; each of which is unfused; each $R^{11}$ is alkyl which is unsubstituted or substituted with $R^{12}$; each $R^{12}$ is $R^{14}$ or $R^{15}$; each of which is unfused; $R^{14}$ is heteroaryl and $R^{15}$ is cycloalkyl each of which is unfused.

In another embodiment of Formula III, $A^1$ is selected from the group consisting of

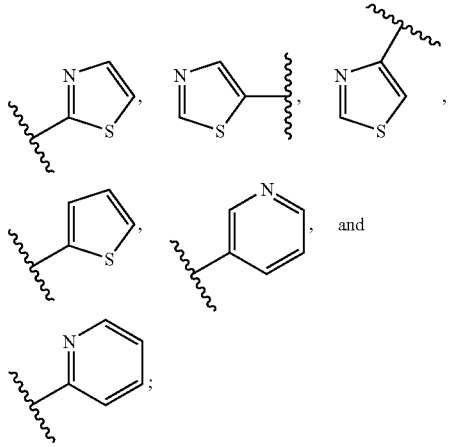

wherein $A^2$ is selected from the group consisting of

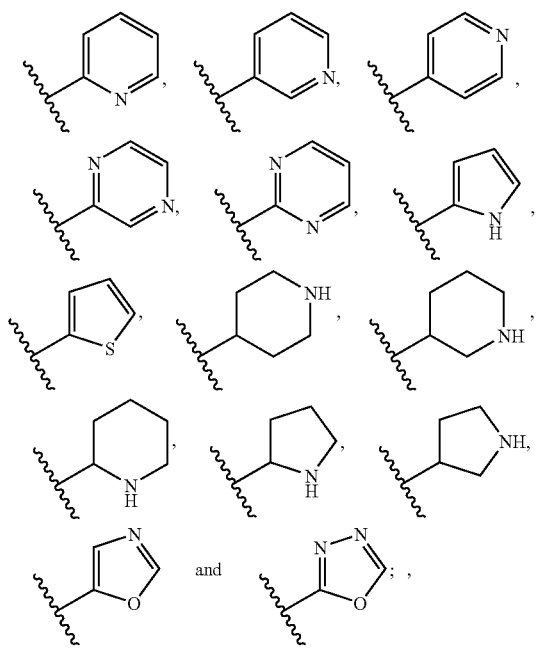

each of which is unfused; wherein $A^1$ and $A^2$ are unsubstituted or substituted with $R^7$ or $CF_3$ as described in Formula III; each $R^7$ is $R^{10}$ or $R^{11}$; $R^{10}$ is cycloalkyl or heterocycloalkyl; each of which is unfused; each $R^{11}$ is alkyl which is unsubstituted or substituted with $R^{12}$; each $R^{12}$ is $R^{14}$ or $R^{15}$; each of which is unfused; $R^{14}$ is heteroaryl and $R^{15}$ is cycloalkyl each of which is unfused.

Schemes

The starting materials used herein are commercially available or may be prepared by routine methods well known to those of ordinary skill in the art. The compounds of the present invention may be prepared using the methods illustrated in the general synthetic schemes and experimental procedures detailed below. The general synthetic schemes are presented for purposes of illustration and are not intended to be limiting.

SCHEME 1

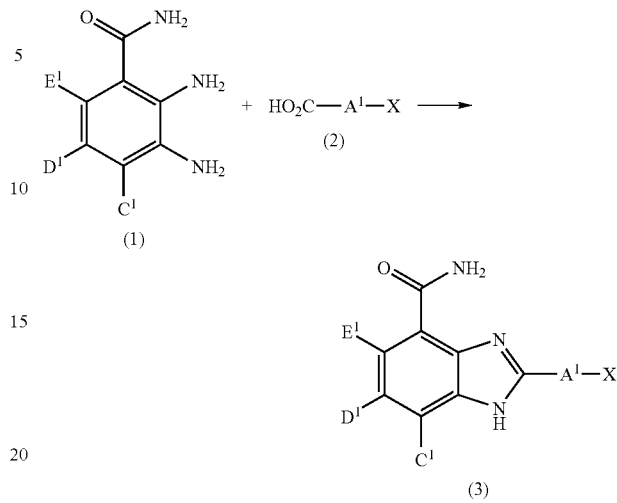

As shown in SCHEME 1, compounds having formula (1) can be converted to compounds having formula (3) by reacting the former, compounds having Formula (2), wherein X is H, I, Br, Cl, or $OSO_2CF_3$, 1,1'-carbonyldiimidazole and pyridine followed by reacting the product therefrom and glacial acetic acid.

SCHEME 2

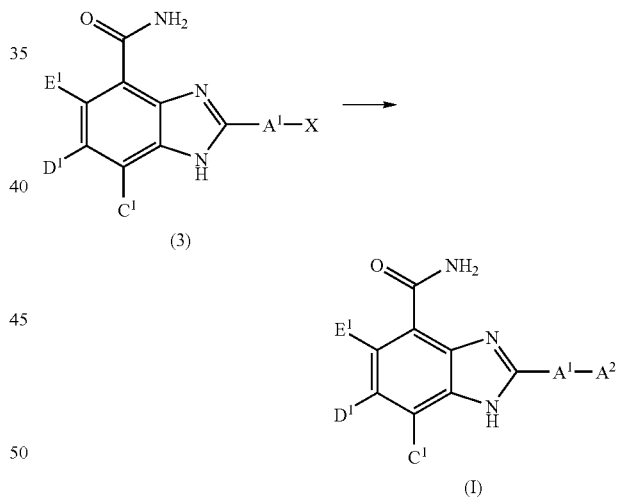

As shown in SCHEME 2, compounds having formula (3) wherein X is I, Br, Cl, or $OSO_2CF_3$, can be converted to compounds having Formula I using methods such as those described in Palladium Reagents And Catalysts: New Perspectives For The 21st Century, By J. Tsuji, John Wiley & Sons, Ltd., Chichester, 2004, 1-670.

SCHEME 3

As shown in SCHEME 3, compounds having formula (2) can be converted to compounds having formula (5) using methods such as those described in Tsuji, op. cit.

SCHEME 4

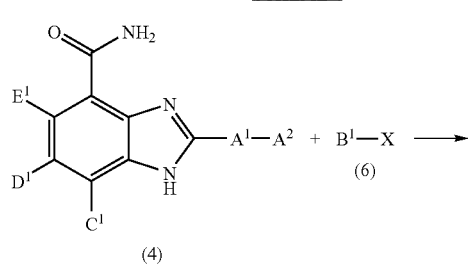

(4)

(I)

As shown in SCHEME 4, compounds having formula (4) can be converted to compounds having Formula I by reacting the former, compounds having formula (6), and a base. Bases include sodium hydride, potassium carbonate and the like. The reaction is typically run in a solvent such as DMF or THF at low temperatures between about 0° C. and 25° C.

The following examples are presented to provide what is believed to be the most useful and readily understood description of procedures and conceptual aspects of this invention.

Example 1

2-(4-pyridin-3-yl-1,3-thiazol-2-yl)-1H-benzimidazole-4-carboxamide

To a mixture of 2-(3-pyridyl)-1,3-thiazole-4-carboxylic acid (300 mg) in pyridine (5 mL) and DMF (5 mL) at ambient temperature was added CDI (248 mg). The mixture was heated at 40° C. for 2 hours, treated with 2,3-diaminobenzamide dihydrochloride (326 mg), stirred at ambient temperature for 16 hours and concentrated. The concentrate was heated in glacial acetic acid (20 mL) at 110° C. for 2 hours, cooled and concentrated. The concentrate was partitioned between ethyl acetate and sodium bicarbonate solution, and the solid that precipitated was filtered and washed with water and ethyl acetate. $^1$H NMR (DMSO-$d_6$) δ 7.38 (t, J=7.8 Hz, 1H), 7.60-7.67 (m, 1H), 7.78 (d, J=7.8 Hz, 1H), 7.81 (brs, 1H), 7.90 (dd, J=7.46, 1.0 Hz, 1H), 8.44-8.50 (m, 1H), 8.74-8.76 (m, 1H), 8.74 (s, 1H), 9.29 (brs, 1H), 9.34 (d, J=1.7 Hz, 1H), 13.44 (brs, 1H).

Example 2

2-(4-pyridin-4-yl-1,3-thiazol-2-yl)-1H-benzimidazole-4-carboxamide

This example was prepared as described in EXAMPLE 1, substituting 2-(4-pyridyl)-1,3-thiazole-4-carboxylic acid for 2-(3-pyridyl)-1,3-thiazole-4-carboxylic acid. $^1$H NMR (DMSO-$d_6$) δ 7.38 (t, J=7.8 Hz, 1H), 7.78 (d, J=8.1 Hz, 1H), 7.83 (brs, 1H), 7.91 (d, J=7.8 Hz, 1H), 8.05-8.06 (m, 1H), 8.07-8.08 (m, 1H), 8.80-8.81 (m, 1H), 8.81-8.83 (m, 2H), 9.28 (brs, 1H), 13.48 (brs, 1H).

Example 3

2-(4-methyl-2-pyrazin-2-yl-1,3-thiazol-5-yl)-H-benzimidazole-4-carboxamide

This example was prepared as described in EXAMPLE 1, substituting 4-methyl-2-(2-pyrazinyl)-1,3-thiazole-5-carboxylic acid for 2-(3-pyridyl)-1,3-thiazole-4-carboxylic acid. $^1$H NMR (DMSO-$d_6$) δ 2.89 (s, 3H) 7.37 (t, J=7.8 Hz, 1H), 7.75 (s, 1H), 7.77 (brs, 1H), 7.89 (d, J=7.7 Hz, 1H), 8.74-8.76 (m, 1H), 8.78 (d, J=2.8 Hz, 1H), 9.08 (brs, 1H), 9.34 (d, J=1.5 Hz, 1H), 13.09 (brs, 1H).

Example 4

2-(2-thien-2-yl-1,3-thiazol-4-yl)-1H-benzimidazole-4-carboxamide

This example was prepared as described in EXAMPLE 1, substituting 2-(2-thienyl)-1,3-thiazole-4-carboxylic acid for 2-(3-pyridyl)-1,3-thiazole-4-carboxylic acid. $^1$H NMR (DMSO-$d_6$) δ 7.23 (t, J=4.3 Hz, 1H), 7.36 (t, J=7.7 Hz, 1H), 7.75 (d, J=7.7 Hz, 1H), 7.78 (d, J=2.5 Hz, 1H), 7.81 (s, 1H), 7.82 (brs, 1H), 7.89 (d, J=7.4 Hz, 1H), 8.57 (s, 1H), 9.27 (brs, 1H), 13.30 (brs, 1H).

Example 5

2-(2-piperidin-4-yl-1,3-thiazol-4-yl)-1H-benzimidazole-4-carboxamide

To a solution of 2-(1-(tertert-butoxycarbonyl)piperid-4-yl)-1,3-thiazole-4-carboxylic acid (1.03 g) in pyridine (8 mL) and DMF (8 mL) at ambient temperature was added CDI (562 mg). The mixture was heated at 40° C. for 2 hours, treated with 2,3-diaminobenzamide dihydrochloride (739 mg), stirred at ambient temperature for 16 hours and concentrated. The concentrate was stirred in glacial acetic acid (30 mL) at 110° C. for 2 hours, cooled and concentrated. The concentrate was stirred in dichloromethane (20 mL) and TFA (8 mL) at ambient temperature for 1 hour, treated with acetonitrile and concentrated. The concentrate was purified by HPLC (Zorbax C-8, 0.1% TFA/acetonitrile/water). The product was dissolved in dichloromethane (5 mL) and methanol (5 mL), treated with 1M hydrochloric acid in ether (10 mL) and concentrated $^1$H NMR (DMSO-$d_6$) δ 1.93-2.09 (m, 2H), 2.26-2.37 (m, 2H), 3.02-3.16 (m, 2H), 3.38-3.47 (m, 2H), 3.49-3.55 (m, 1H), 7.38 (t, J=7.8 Hz, 1H), 7.77 (d, J=7.1 Hz, 1H), 7.80 (s, 1H), 7.90 (d, J=7.5 Hz, 1H), 8.64 (s, 1H), 8.72 (brs, 1H), 8.94 (brs, 1H), 9.11 (brs, 1H).

Example 6

2-(2-(1-methylpiperidin-4-yl)-1,3-thiazol-4-yl)-1H-benzimidazole-4-carboxamide

To a solution of EXAMPLE 5 (50 mg) in methanol (8 mL) was added 37 wt % formaldehyde in water (28 μL) and TEA (21 μL). The solution was stirred for 1 hour, treated with sodium cyanoborohydride (28 mg) and zinc (II) chloride (20 mg), stirred for 60 hours and was concentrated. The concentrate was purified by HPLC (Zorbax C-8, 0.1% TFA/acetonitrile/water). The salt was dissolved in dichloromethane (2 mL) and methanol (2 mL), treated with 1M hydrochloric acid in ether (4 mL) and concentrated. $^1$H NMR (DMSO-d$_6$) δ 2.12-2.23 (m, 2H), 2.32-2.41 (m, 2H), 2.78 (d, J=4.6 Hz, 3H), 3.10-3.20 (m, 2H), 3.41-3.48 (m, 1H), 3.50-3.59 (m, 2H), 7.45 (t, J=7.8 Hz, 1H), 7.80-7.82 (m, 1H), 7.82-7.85 (m, 1H), 7.94 (d, J=6.7 Hz, 1H), 8.82 (brs, 1H), 8.98 (brs, 1H), 10.84 (brs, 1H).

Example 7

2-(2-(1-isopropylpiperidin-4-yl)-1,3-thiazol-4-yl)-1H-benzimidazole-4-carboxamide This example was prepared as the hydrochloride salt as described in EXAMPLE 6, substituting acetone for formaldehyde. $^1$H NMR (DMSO-d$_6$) δ 1.33 (d, J=6.7 Hz, 6H), 2.27-2.43 (m, 4H), 3.12-3.23 (m, 2H), 3.46-3.56 (m, 4H), 7.46 (t, J=7.8 Hz, 1H), 7.80-7.83 (m, 1H), 7.83-7.87 (m, 1H), 7.94 (d, J=7.6 Hz, 1H), 8.85 (brs, 1H), 8.97 (brs, 1H), 10.68 (brs, 1H).

Example 8

2-(2-(1-propylpiperidin-4-yl)-1,3-thiazol-4-yl)-1H-benzimidazole-4-carboxamide This example was prepared as the hydrochloride salt as described in EXAMPLE 6, substituting propionaldehyde for formaldehyde. $^1$H NMR (DMSO-d$_6$) δ 0.94 (t, J=7.3 Hz, 3H), 1.73-1.83 (m, 2H), 2.17-2.28 (m, 2H), 2.33-2.40 (m, 2H), 2.97-3.05 (m, 2H), 3.05-3.17 (m, 2H), 3.43-3.51 (m, 1H), 3.56-3.65 (m, 2H), 7.44 (t, J=7.8 Hz, 1H), 7.79-7.82 (m, 1H), 7.82-7.85 (m, 1H), 7.93 (d, J=7.6 Hz, 1H), 8.79 (brs, 1H), 9.00 (brs, 1H), 10.69 (brs, 1H).

Example 9

2-(2-(1-cyclobutylpiperidin-4-yl)-1,3-thiazol-4-yl)-1H-benzimidazole-4-carboxamide This example was prepared as the hydrochloride salt as described in EXAMPLE 6, substituting cyclobutanone for formaldehyde. $^1$H NMR (DMSO-d$_6$) δ 1.71-1.81 (m, 2H), 2.16-2.26 (m, 4H), 2.33-2.41 (m, 3H), 2.42-2.48 (m, 2H), 2.89-2.98 (m, 2H), 3.44-3.50 (m, 2H), 3.60-3.67 (m, 1H), 7.45 (t, J=7.8 Hz, 1H), 7.79-7.82 (m, 1H), 7.82-7.86 (m, 1H), 7.94 (d, J=7.0 Hz, 1H), 8.82 (brs, 1H), 8.98 (brs, 1H), 11.24 (brs, 1H).

Example 10

2-(5-pyridin-2-ylthien-2-yl)-1H-benzimidazole-4-carboxamide

Example 10A

2-(5-bromothiophen-2-yl)-1H-benzimidazole-4-carboxamide

This example was prepared as described in EXAMPLE 1, substituting 5-bromo-2-thiophenecarboxylic acid for 2-(3-pyridyl)-1,3-thiazole-4-carboxylic acid. $^1$H NMR (DMSO-d$_6$) δ 7.33 (brs, 1H), 7.39 (d, J=3.1 Hz, 1H), 7.71 (m, 3H), 7.84 (brs, 1H), 8.99 (brs, 1H), 13.48 (brs, 1H).

Example 10B

2-(5-pyridin-2-ylthien-2-yl)-1H-benzimidazole-4-carboxamide

A mixture of EXAMPLE 10A (184 mg), tri-ortho-tolylphosphine (52 mg), tris(dibenzylidineacetone)dipalladium(0) (52 mg), 2-(tri-n-butylstannyl)pyridine (420 mg) and triethylamine (238 L) in DMF (5 mL) was heated at 75° C. overnight. The mixture was cooled, diluted with dichloromethane and flash chromatographed (with 0-15% methanol in 2:1 ethyl acetate/hexane). Additional purification by HPLC (Zorbax, C-18, Mobile phase A: 0.1% TFA in H$_2$O; B: 0.1% TFA in acetonitrile; 0-100% gradient) provided the title compound. $^1$H NMR (DMSO-d$_6$) δ 7.34-7.39 (m, 2H), 7.74-7.76 (m, 2H), 7.86-7.95 (m, 3H), 8.00-8.05 (m, 1H), 8.02 (s, 1H), 8.60 (d, J=4.6 Hz, 1H), 9.04 (brs, 1H).

Example 11

2-(5-pyrazin-2-ylthien-2-yl)-1H-benzimidazole-4-carboxamide

This example was prepared as the trifluoroacetate salt as described in EXAMPLE 10B, substituting 2-(tri-n-butylstannyl)pyrazine for 2-(tri-n-butylstannyl)pyridine. $^1$H NMR (DMSO-d$_6$) δ 7.35 (t, J=7.8 Hz, 1H), 7.73 (s, 1H), 7.75 (d, J=7.7 Hz, 1H), 7.86 (d, J=7.7 Hz, 1H), 8.03 (d, J=3.7 Hz, 1H), 8.09 (d, J=4.0 Hz, 1H), 8.57 (d, J=2.4 Hz, 1H), 8.63 (s, 1H), 8.99 (s, 1H), 9.31 (d, J=1.2 Hz, 1H).

Example 12

2-(5-pyrimidin-2-ylthien-2-yl)-1H-benzimidazole-4-carboxamide

This example was prepared as the trifluoroacetate salt as described in EXAMPLE 10B, substituting 2-(tri-n-butylstannyl)pyrimidine for 2-(tri-n-butylstannyl)pyridine. $^1$H NMR (DMSO-d$_6$) δ 7.37 (t, J=7.8 Hz, 1H), 7.44 (t, J=4.9 Hz, 1H), 7.75 (s, 1H), 7.77 (d, J=7.4 Hz, 1H), 7.88 (d, J=7.4 Hz, 1H), 8.02-8.06 (m, 2H), 8.87 (d, J=4.9 Hz, 2H), 9.04 (s, 1H).

Example 13

2-(5-pyridin-3-ylthien-2-yl)-1H-benzimidazole-4-carboxamide

This example was prepared as the trifluoroacetate salt as described in EXAMPLE 10B, substituting 3-(tri-n-butylstannyl)pyridine for 2-(tri-n-butylstannyl)pyridine. $^1$H NMR (DMSO-d$_6$) δ 7.37 (t, J=7.6 Hz, 1H), 7.67 (dd, J=7.9, 4.9 Hz, 1H), 7.76 (d, J=7.9 Hz, 1H), 7.82 (s, 1H), 7.87 (d, J=4.0 Hz, 1H), 7.88 (s, 1H), 8.05 (d, J=3.7 Hz, 1H), 8.39 (d, J=8.24 Hz, 1H), 8.65 (d, J=4.9 Hz, 1H), 8.99 (brs, 1H), 9.13 (d, J=2.1 Hz, 1H).

Example 14

2-(5-pyridin-4-ylthien-2-yl)-1H-benzimidazole-4-carboxamide

This example was prepared as the trifluoroacetate salt as described in EXAMPLE 10B, substituting 4-(tri-n-butylstannyl)pyridine for 2-(tri-n-butylstannyl)pyridine. $^1$H NMR (DMSO-d$_6$) δ 7.38 (t, J=7.7 Hz, 1H), 7.78 (d, J=7.1 Hz, 1H), 7.81 (brs, 1H), 7.88 (d, J=7.7 Hz, 1H), 8.11 (d, J=6.4 Hz, 2H), 8.16 (d, J=7.7 Hz, 1H), 8.77 (d, J=6.4 Hz, 2H), 8.94 (brs, 1H).

Example 15

2-(5-(1H-pyrrol-2-yl)thien-2-yl)-1H-benzimidazole-4-carboxamide

To EXAMPLE 10A (100 mg), 1-(tert-butoxycarbonyl)pyrrole-2-boronic acid (100 mg) and dichlorobis(triphenylphosphine)palladium(II) (21 mg) in 1,2-dimethoxyethane/water/ethanol (7/3/2, 10 mL) was added 2M sodium carbonate solution (1.5 mL). The mixture was heated at 80° C. for 1 hour and concentrated. The concentrate was partitioned between ethyl acetate and brine, and the organic phase was washed with brine, dried over magnesium sulfate, filtered and concentrated. The concentrate in THF (10 mL) was treated TFA (1 mL) and stirred overnight and concentrated. The concentrate was purified by HPLC (Zorbax, C-18, Mobile phase A: 0.1% TFA in water; B: 0.1% TFA in acetonitrile; 0-100% gradient). $^1$H NMR (DMSO-d$_6$) δ 6.15-6.17 (m, 1H), 6.53-6.54 (m, 1H), 6.93-6.94 (m, 1H), 7.19-7.43 (m, 3H), 7.72 (d, J=7.0 Hz, 1), 7.79 (s, 1H), 7.85 (d, J=7.6 Hz, 1H), 7.92 (d, J=3.7 Hz, 1H), 9.02 (s, 1H), 11.57 (s, 1H).

Example 16

2-(5-((2R)-pyrrolidin-2-yl)thien-2-yl)-1H-benzimidazole-4-carboxamide

Example 16A (R)-tert-butyl 2-(5-methoxycarbonylthiophen-2-yl)pyrrolidine-1-carboxylate To a solution of N-Boc-pyrrolidine (3 mL) and (−)-sparteine (3.9 mL) in tert-butyl methyl ether (36 mL) at −78° C. was added 1.4M sec-butyl lithium in cyclohexane (12.21 mL). The solution was stirred for 3 hours and 1M zinc chloride in ether (10.2 mL) was added. The mixture was stirred for 30 minutes and warmed to ambient temperature for 30 minutes. Methyl 5-bromothiophene-2-carboxylate (3.15 g), tri-tert-butylphosphine tetrafluoroborate (249 mg) and palladium(II) acetate (153 mg) were added, and the mixture was stirred at ambient temperature overnight, treated with concentrated ammonium hydroxide (1 mL) and stirred for 30 minutes, and filtered through diatomaceous earth (Celite®). The filtrate was washed with 0.5M hydrochloric acid solution and water and concentrated. The concentrate was flash chromatographed on silica gel with ethyl acetate/hexane.

Example 16B (R)-2-(5-carboxythiophen-2-yl)pyrrolidine-1-carboxylic acid tert-butyl ester To a mixture of EXAMPLE 16A (2.8 g) in THF (20 mL) was added lithium hydroxide monohydrate (500 mg) in water (5 mL). The mixture stirred at ambient temperature overnight and partitioned between ethyl acetate and 0.5 M hydrochloric acid. The extract was washed with water, dried over magnesium sulfate, filtered and concentrated.

Example 16C (R)-tert-butyl 2-(5-(4-carbamoyl-1H-benzimidazol-2-yl)thiophen-2-yl)pyrrolidine-1-carboxylate To a solution of EXAMPLE 16B (2.4 g) in pyridine (20 mL) and DMF (20 mL) was added CDI (1.6 g), and the mixture was stirred at 40° C. for 1 hour. 2,3-Diaminobenzamide dihydrochloride (1.8 g) was added, and the mixture stirred at ambient temperature overnight and concentrated. The concentrate was stirred in of acetic acid (20 mL) at 80° C. for 4 hours and concentrated. The concentrate was partitioned between ethyl acetate and saturated sodium bicarbonate solution, and the extract was washed with water and concentrated. The concentrate was purified by flash chromatography on silica gel with 40-80% ethyl acetate in hexane.

Example 16D 2-(5-((2R)-pyrrolidin-2-yl)thien-2-yl)-1H-benzimidazole-4-carboxamide A solution of EXAMPLE 16C (2.2 g) in TFA (50 mL) was stirred at ambient temperature for 30 minutes. After concentration, the concentrate was purified by HPLC (Zorbax, C-18, Mobile phase A: 0.1% TFA in water; B: 0.1% TFA in acetonitrile; 0-100% gradient). $^1$H NMR (CD$_3$OD) δ 2.19-2.29 (m, 1H), 2.28-2.41 (m, 2H), 2.55-2.67 (m, 1H), 3.43-3.56 (m, 2H), 5.01 (dd, J=9.3, 6.9 Hz, 1H), 7.36 (d, J=3.7 Hz, 1H), 7.39 (d, J=4.6 Hz, 1H), 7.71 (d, J=7.6 Hz, 1H), 7.79 (d, J=3.7 Hz, 1H), 7.93 (d, J=7.6 Hz, 1H).

Example 17

2-(5-((2R)-1-methylpyrrolidin-2-yl)thien-2-yl)-1H-benzimidazole-4-carboxamide

A solution of EXAMPLE 16D (50 mg) in methanol (20 mL) was treated with 37 wt % formaldehyde in water (114 μL) and stirred overnight. Sodium cyanoborohydride (315 mg) was added, and the solution was stirred for 3 hours and concentrated. The concentrate was dissolved in methanol and TFA, and purified by HPLC (Zorbax C-8, 0.1% TFA/acetonitrile/water). $^1$H NMR (CD$_3$OD) δ 2.30 (m, 2H), 2.47 (m, 1H), 2.74 (m, 1H), 2.94 (s, 3H), 3.31-3.40 (m, 1H), 3.88 (m, 1H), 4.81 (m, 1H), 7.40 (t, J=7.7 Hz, 1H), 7.51 (d, J=3.7 Hz, 1H), 7.73 (d, J=7.6 Hz, 1H), 7.86 (d, J=4.0 Hz, 1H), 7.95 (d, J=7.6 Hz, 1H).

Example 18

2-(5-((2R)-1-isopropylpyrrolidin-2-yl)thien-2-yl)-1H-benzimidazole-4-carboxamide This example was prepared as the trifluoroacetate salt as described in EXAMPLE 17, substituting acetone for formaldehyde. $^1$H NMR (CD$_3$OD) δ 1.40 (dd, J=11.6, 6.7 Hz, 6H), 2.26-2.31 (m, 2H), 2.35-2.48 (m, 1H), 2.62-2.68 (m, 1H), 3.40-3.47 (m, 1H), 3.55-3.73 (m, 2H), 4.98-5.10 (m, 1H), 7.39 (t, J=7.8 Hz, 1H), 7.50 (d, J=4.0 Hz, 1H), 7.74 (d, J=8.2 Hz, 1H), 7.84 (d, J=4.0 Hz, 1H), 7.95 (d, J=7.6 Hz, 1H).

Example 19

2-(5-((2R)-1-propylpyrrolidin-2-yl)thien-2-yl)-1H-benzimidazole-4-carboxamide

This example was prepared as the trifluoroacetate salt as described in EXAMPLE 17, substituting propionaldehyde for formaldehyde. $^1$H NMR (CD$_3$OD) δ 0.99 (t, J=6.9 Hz, 3H), 1.59-1.73 (m, 1H), 1.75-1.85 (m, 1H), 2.25-2.37 (m, 2H), 2.36-2.49 (m, 1H), 2.60-2.75 (m, 1H), 3.02-3.13 (m, 1H), 3.18-3.30 (m, 1H), 3.31-3.42 (m, 1H), 3.80-3.98 (m, 1H), 4.78-4.89 (m, 1H), 7.40 (t, J=7.8 Hz, 1H), 7.51 (d, J=4.0 Hz, 1H), 7.74 (d, J=7.9 Hz, 1H), 7.86 (d, J=4.0 Hz, 1H), 7.95 (d, J=6.7 Hz, 1H).

Example 20

2-(5-((2R)-1-(cyclopropylmethyl)pyrrolidin-2-yl)thien-2-yl)-1H-benzimidazole-4-carboxamide This example was prepared as the trifluoroacetate salt as described in EXAMPLE 17, substituting cyclopropanecarbaldehyde for formaldehyde. $^1$H NMR (CD$_3$OD) δ 0.24-0.33 (m, 1H), 0.40-0.45 (m, 1H), 0.65-0.79 (m, 2H), 1.01-1.17 (m, 2H), 2.26-2.38 (m, 2H), 2.38-2.49 (m, 1H), 2.63-2.76 (m, 1H), 3.03-3.10 (m, 1H), 3.11-3.20 (m, 1H), 3.38-3.49 (m, 1H), 3.95-4.05 (m, 1H), 7.39 (t, J=7.8 Hz, 1H), 7.49 (d, J=3.7 Hz, 1H), 7.74 (d, J=7.9 Hz, 1H), 7.84 (d, J=4.0 Hz, 1H), 7.95 (d, J=7.6 Hz, 1H).

Example 21

2-(5-((2R)-1-cyclobutylpyrrolidin-2-yl)thien-2-yl)-1H-benzimidazole-4-carboxamide This example was prepared as the trifluoroacetate salt as described in EXAMPLE 17, substituting cyclobutanone for formaldehyde. $^1$H NMR (CD$_3$OD) δ 1.76-1.89 (m, 2H), 1.95-2.04 (m, 1H), 2.12-2.22 (m, 1H), 2.23-2.35 (m, 4H), 2.40-2.45 (m, 1H), 2.63-2.76 (m, 1H), 3.25-3.36 (m, 2H), 3.70-3.75 (m, 1H), 3.93-4.05 (m, 1H), 7.39 (t, J=7.8 Hz, 1H), 7.47 (d, J=3.7 Hz, 1H), 7.74 (d, J=8.2 Hz, 1H), 7.82 (d, J=4.0 Hz, 1H), 7.95 (d, J=7.6 Hz, 1H).

Example 22

2-(5-((2R)-1-cyclopentylpyrrolidin-2-yl)thien-2-yl)-1H-benzimidazole-4-carboxamide This example was prepared as the trifluoroacetate salt as described in EXAMPLE 17, substituting cyclopentanone for formaldehyde. $^1$H NMR (CD$_3$OD) δ 1.60-1.69 (m, 2H), 1.73-1.91 (m, 3H), 2.02-2.13 (m, 1H), 2.12-2.24 (m, 1H), 2.27-2.36 (m, 2H), 2.35-2.48 (m, 2H), 2.60-2.74 (m, 1H), 3.38-3.54 (m, 1H), 3.66-3.76 (m, 1H), 3.78-3.89 (m, 1H), 4.94-5.07 (m, 1H), 7.39 (t, J=7.9 Hz, 1H), 7.49 (d, J=4.0 Hz, 1H), 7.74 (d, J=8.2 Hz, 1H), 7.83 (d, J=4.0 Hz, 1H), 7.95 (d, J=7.6 Hz, 1H).

Example 23

2-(5-((2R)-1-cyclohexylpyrrolidin-2-yl)thien-2-yl)-1H-benzimidazole-4-carboxamide This example was prepared as the trifluoroacetate salt as described in EXAMPLE 17, substituting cyclohexanone for formaldehyde. $^1$H NMR (CD$_3$OD) δ 1.17-1.26 (m, 1H), 1.27-1.45 (m, 2H), 1.45-1.68 (m, 3H), 1.67-1.95 (m, 2H), 1.85-1.93 (m, 1H), 1.94-2.09 (m, 2H), 2.10-2.20 (m, 1H), 2.22-2.34 (m, 1H), 2.34-2.47 (m, 1H), 2.59-2.72 (m, 1H), 3.44-3.55 (m, 1H), 3.59-3.71 (m, 1H), 5.10-5.20 (m, 1H), 7.39 (t, J=7.9 Hz, 1H), 7.50 (d, J=3.7 Hz, 1H), 7.74 (d, J=7.0 Hz, 1H), 7.85 (d, J=4.0 Hz, 1H), 7.95 (d, J=7.6 Hz, 1H).

Example 24

2-(5-((2R)-1-tetrahydro-2H-pyran-4-ylpyrrolidin-2-yl)thien-2-yl)-1H-benzimidazole-4-carboxamide This example was prepared as the trifluoroacetate salt as described in EXAMPLE 17, substituting tetrahydro-pyran-4-one for formaldehyde. $^1$H NMR (CD$_3$OD) δ 1.70-1.77 (m, 1H), 1.77-1.91 (m, 2H), 1.95-2.03 (m, 1H), 2.05-2.19 (m, 1H), 2.25-2.37 (m, 1H), 2.37-2.50 (m, 2H), 2.57-2.75 (m, 1H), 3.37-3.51 (m, 1H), 3.59-3.74 (m, 2H), 3.90-3.97 (m, 1H), 3.97-4.04 (m, 1H), 4.04-4.12 (m, 1H), 5.10-5.19 (m, 1H), 7.40 (t, J=7.9 Hz, 1H), 7.52 (d, J=3.7 Hz, 1H), 7.74 (d, J=7.0 Hz, 1H), 7.85 (d, J=4.0 Hz, 1H), 7.95 (d, J=7.6 Hz, 1H).

Example 25

2-(5-((2R)-1-(pyridin-2-ylmethyl)pyrrolidin-2-yl)thien-2-yl)-1H-benzimidazole-4-carboxamide This example was prepared as the trifluoroacetate salt as described in EXAMPLE 17, substituting pyridine-2-carbaldehyde for formaldehyde. $^1$H NMR (CD$_3$OD) δ 2.25-2.38 (m, 2H), 2.42-2.54 (m, 1H), 2.66-2.80 (m, 1H), 3.39-3.52 (m, 1H), 3.68-3.79 (m, 1H), 4.42 (d, J=7.7 Hz, 1H), 4.55 (d, J=7.7 Hz, 1H), 5.09 (dd, J=9.8, 7.3 Hz, 1H), 7.38 (d, J=3.7 Hz, 1H), 7.40 (t, J=7.9 Hz, 1H), 7.41-7.46 (m, 1H), 7.48 (d, J=7.6 Hz, 1H), 7.69-7.75 (m, 1H), 7.77 (d, J=4.0 Hz, 1H), 7.84-7.92 (m, 1H), 7.95 (dd, J=7.6, 1.2 Hz, 1H), 8.63 (d, J=4.0 Hz, 1H).

Example 26

2-(5-((2R)-1-(pyridin-4-ylmethyl)pyrrolidin-2-yl)thien-2-yl)-1H-benzimidazole-4-carboxamide This example was prepared as the trifluoroacetate salt as described in EXAMPLE 17, substituting pyridine-4-carbaldehyde for formaldehyde. $^1$H NMR (CD$_3$OD) δ 2.03-2.21 (m, 3H), 2.40-2.58 (m, 1H), 2.65-2.80 (m, 1H), 3.31-3.38 (m, 1H), 3.98 (d, J=15.6 Hz, 1H), 4.34 (d, J=15.6 Hz, 1H), 4.39 (t, J=7.0 Hz, 1H), 7.28 (d, J=3.7 Hz, 1H), 7.41 (t, J=7.8 Hz, 1H), 7.74 (d, J=7.0 Hz, 1H), 7.79 (d, J=4.0 Hz, 1H), 7.94 (d, J=7.6 Hz, 1H), 8.00 (d, J=6.4 Hz, 2H), 8.73 (d, J=6.7 Hz, 2H).

Example 27

2-(5-((2R)-1-isobutylpyrrolidin-2-yl)thien-2-yl)-1H-benzimidazole-4-carboxamide

This example was prepared as the trifluoroacetate salt as described in EXAMPLE 17, substituting 2-methyl-propionaldehyde for formaldehyde. $^1$H NMR (CD$_3$OD) δ 1.00 (dd, J=13.7, 6.7 Hz, 6H), 2.01-2.13 (m, 1H), 2.28-2.38 (m, 2H), 2.38-2.52 (m, 1H), 2.59-2.74 (m, 1H), 3.00-3.12 (m, 2), 3.32-3.41 (m, 1H), 3.90-4.12 (m, 1H), 4.80-4.92 (m, 1H), 7.40 (t, J=7.8 Hz, 1H), 7.52 (d, J=3.7 Hz, 1H), 7.75 (d, J=7.9 Hz, 1H), 7.86 (d, J=4.0 Hz, 1H), 7.96 (d, J=7.6 Hz, 1H).

Example 28

2-(5-piperidin-2-ylthien-2-yl)-1H-benzimidazole-4-carboxamide

Example 28A methyl 5-(pyridin-2-yl)thiophene-2-carboxylate

To methyl 5-bromo-thiophene-2-carboxylate (2 g), tri-2-furylphosphine (400 mg), and tris(dibenzylidineacetone)dipalladium(0) (400 mg) was added DMF (50 mL), 2-(tributylstannyl)pyridine (4 g) and TEA (1 mL) The mixture was heated at 80° C. for 7 hours, cooled and partitioned between ethyl acetate and brine. The aqueous phase was extracted with ethyl acetate, and the extract was dried, filtered and concentrated. The concentrate was flash chromatographed on silica gel with a 20-70% ethyl acetate in hexane.

Example 28B methyl 5-(piperidin-2-yl)thiophene-2-carboxylate

EXAMPLE 28A (1.7 g) in methanol (100 mL) and 10% palladium on carbon (170 mg) was stirred under 60 psi of hydrogen until all starting material was consumed, filtered and concentrated.

Example 28C benzyl 2-(5-(methoxycarbonyl)thiophen-2-yl)piperidine-1-carboxylate To a mixture of EXAMPLE 28B (0.3 g), potassium carbonate (0.36 g), dioxane (20 mL) and water (5 mL) was added benzyl chloroformate (0.23 mL), and the mixture stirred for 4 hours. Piperazine was added, and the mixture stirred for 30 minutes and partitioned between ethyl acetate and brine. The extract was washed with brine, dried over magnesium sulfate, filtered and concentrated. The concentrate was flash chromatographed on silica gel with 10-50% ethyl acetate in hexane.

Example 28D 5-(1-(benzyloxycarbonyl)piperidin-2-yl)thiophene-2-carboxylic acid To EXAMPLE 28C (0.4 g) in THF (10 mL) was added lithium hydroxide hydrate (132 mg) in water (3 mL). The mixture was stirred at ambient temperature overnight and partitioned between ethyl acetate and 0.5 M hydrochloric acid. The extract was washed with water, dried over magnesium sulfate, filtered, and concentrated. The concentrate was flash chromatographed silica gel with ethyl acetate.

Example 28E benzyl 2-(5-(4-carbamoyl-1H-benzimidazol-2-yl)thiophen-2-yl)piperidine-1-carboxylate To a solution of EXAMPLE 28D (0.35 g) in pyridine (10 mL) and DMF (10 mL) was added CDI (0.23 g), and the mixture was heated at 40° C. for 1 hour. 2,3-Diaminobenzamide dichloride (0.22 g) was added, and the mixture stirred at ambient temperature overnight and concentrated. The concentrate was stirred in acetic acid (20 mL) at 80° C. for 4 hours and concentrated. The concentrate was partitioned between ethyl acetate and saturated sodium bicarbonate solution. The extract was washed with water and concentrated, and the concentrate was flash chromatographed on silica gel with 40-80% ethyl acetate in hexane.

Example 28F 2-(5-piperidin-2-ylthien-2-yl)-1H-benzimidazole-4-carboxamide

A solution of EXAMPLE 28E (0.21 g) in TFA (10 mL) was stirred at ambient temperature overnight and concentrated. The concentrate was purified by HPLC (Zorbax, C-18, Mobile phase A: 0.1% TFA in water; B: 0.1% TFA in acetonitrile; 0-100% gradient). $^1$H NMR (DMSO-$d_6$) δ 1.62-1.76 (m, 1H), 1.84-1.96 (m, 2H), 2.00-2.08 (m, 1H), 2.10-2.20 (m, 1H), 2.19-2.28 (m, 1H), 3.06-3.13 (m, 1H), 3.34-3.47 (m, 1H), 4.36-4.50 (m, 1H), 7.02 (s, 1H), 7.28 (t, J=7.9 Hz, 1H), 7.38 (d, J=4.0 Hz, 1H), 7.65 (d, J=7.0 Hz, 1H), 7.81 (d, J=4.0 Hz, 1H), 7.98 (d, J=7.3 Hz, 1H), 9.40 (s, 1H), 9.50 (s, 1H), 10.10 (s, 1H).

Example 29

2-(5-(1-methylpiperidin-2-yl)thien-2-yl)-1H-benzimidazole-4-carboxamide

This example was prepared as the trifluoroacetate salt as described in EXAMPLE 17, substituting EXAMPLE 28F for EXAMPLE 16D. $^1$H NMR (CD$_3$OD) δ 1.63-1.86 (m, 1H), 1.86-2.00 (m, 1H), 2.00-2.11 (m, 2H), 2.11-2.23 (m, 1H), 2.30-2.39 (m, 1H), 2.75 (s, 3H), 3.17-3.28 (m, 1H), 3.68-3.73 (m, 1H), 4.58 (dd, J=12.3, 2.8 Hz, 1H), 7.38 (t, J=7.9 Hz, 1H), 7.43 (d, J=3.7 Hz, 1H), 7.75 (dd, J=8.0, 1.2 Hz, 1H), 7.85 (d, J=3.7 Hz, 1H), 7.95 (dd, J=7.7, 1.2 Hz, 1H).

Example 30

2-(5-(1-propylpiperidin-2-yl)thien-2-yl)-1H-benzimidazole-4-carboxamide

This example was prepared as the trifluoroacetate salt as described in EXAMPLE 17, substituting EXAMPLE 28F for EXAMPLE 16D and propionaldehyde for formaldehyde. $^1$H NMR (CD$_3$OD) δ 0.89 (t, J=7.4 Hz, 3H), 1.47-1.63 (m, 1H), 1.70-1.98 (m, 3H), 1.99-2.15 (m, 2H), 2.17-2.23 (m, 1H), 2.26-2.35 (m, 1H), 2.83-2.95 (m, 1H), 2.96-3.10 (m, 1H), 3.10-3.25 (m, 1H), 3.78 (d, J=12.9 Hz, 1H), 4.70 (dd, J=12.0, 2.8 Hz, 1H), 7.36 (t, J=7.6 Hz, 1H), 7.43 (d, J=3.7 Hz, 1H), 7.75 (dd, J=8.0, 1.2 Hz, 1H), 7.85 (d, J=3.7 Hz, 1H), 7.96 (d, J=7.7 Hz, 1H).

Example 31

2-(5-(1-(cyclopropylmethyl)piperidin-2-yl)thien-2-yl)-1H-benzimidazole-4-carboxamide This example was prepared as described in EXAMPLE 17, substituting EXAMPLE 28F for EXAMPLE 16D and cyclopropanecarbaldehyde for formaldehyde. $^1$H NMR (CD$_3$OD) δ 0.22-0.30 (m, 1H), 0.30-0.40 (m, 1H), 0.66-0.81 (m, 2H), 1.00-1.10 (m, 1H), 1.72-1.84 (m, 1H), 1.91-2.15 (m, 3H), 2.15-2.26 (m, 1H), 2.28-2.36 (m, 1H), 2.82-2.90 (m, 1H), 2.95-3.02 (m, 1H), 3.19-3.28 (m, 1H), 4.01 (d, J=13.1 Hz, 1H), 4.69 (dd, J=12.2, 2.7 Hz, 1H), 7.40 (t, J=7.7 Hz, 1H), 7.42 (d, J=3.7 Hz, 1H), 7.75 (dd, J=8.0, 1.2 Hz, 1H), 7.83 (d, J=4.0 Hz, 1H), 7.95 (d, J=7.6 Hz, 1H).

Example 32

2-(5-(1-cyclobutylpiperidin-2-yl)thien-2-yl)-1H-benzimidazole-4-carboxamide

This example was prepared as described in EXAMPLE 17, substituting EXAMPLE 28F for EXAMPLE 16D and cyclobutanone for formaldehyde. $^1$H NMR (CD$_3$OD) δ 1.34-1.48 (m, 1H), 1.51-1.81 (m, 3H), 1.82-2.12 (m, 4H), 2.11-2.37 (m, 4H), 2.88-3.00 (m, 1H), 3.66 (d, J=12.6 Hz, 1H), 3.74-3.88 (m, 1H), 4.60 (dd, J=12.0, 2.8 Hz, 1H), 7.40 (t, J=7.7 Hz, 1H), 7.42 (d, J=3.7 Hz, 1H), 7.74 (dd, J=8.1, 1.1 Hz, 1H), 7.81 (d, J=3.7 Hz, 1H), 7.95 (dd, J=7.5, 1.1 Hz, 1H).

Example 33

2-(5-(1-isobutylpiperidin-2-yl)thien-2-yl)-1H-benzimidazole-4-carboxamide

This example was prepared as described in EXAMPLE 17, substituting EXAMPLE 28F for EXAMPLE 16D and 2-methyl-propionaldehyde for formaldehyde. $^1$H NMR (CD$_3$OD) δ 0.91 (d, J=6.7 Hz, 3H), 0.96 (d, J=6.4 Hz, 3H), 1.00-1.07 (m, 2H), 1.87-1.97 (m, 1H), 1.97-2.11 (m, 4H), 2.92 (d, J=7.1 Hz, 2H), 2.98-3.21 (m, 1H), 3.86 (d, J=12.6 Hz, 1H), 4.57-4.71 (m, 1H), 7.40 (t, J=7.7 Hz, 1H), 7.45 (d, J=4.0 Hz, 1H), 7.74 (dd, J=8.1, 1.1 Hz, 1H), 7.85 (d, J=4.0 Hz, 1H), 7.96 (dd, J=7.7, 1.2 Hz, 1H).

Example 34

2-(5-pyrrolidin-2-ylthien-2-yl)-1H-benzimidazole-4-carboxamide

Example 34A tert-butyl 2-(5-(methoxycarbonyl)thiophen-2-yl)-1H-pyrrole-1-carboxylate A mixture of methyl 5-bromothiophene-2-carboxylate (4 g), 1-(tert-butoxycarbonyl)pyrrole-2-boronic acid (3.8 g), dichlorobis(triphenylphosphine)palladium(II) (1.2 g) and 2M sodium carbonate solution (18 mL) in DME/water/ethanol (7/3/2, 200 mL) was heated at 60° C. for 4 hours, cooled and partitioned between ethyl acetate and brine. The extract was washed with water and concentrated, and the concentrate was flash chromatographed on silica gel with 5-40% ethyl acetate in hexane.

Example 34B tert-butyl 2-(5-(methoxycarbonyl)thiophen-2-yl)pyrrolidine-1-carboxylate To a solution of EXAMPLE 34A (3.7 g) in acetic acid (200 mL) was added 5% platinum on carbon (370 mg). The mixture was shaken under 60 psi of hydrogen until all starting material was consumed, filtered and concentrated. The concentrate was partitioned between ethyl acetate and saturated sodium bicarbonate solution. The extract was washed with water and concentrated.

The concentrate was flash chromatographed on silica gel with 10-30% ethyl acetate in hexane.

Example 34C 5-(1-(tert-butoxycarbonyl)pyrrolidin-2-yl)thiophene-2-carboxylic acid To a mixture of EXAMPLE 34B (2.7 g) in THF (50 mL) was added lithium hydroxide (0.2 g) in water (5 mL). The mixture was stirred at ambient temperature overnight and partitioned between ethyl acetate and 0.5 M hydrochloric acid. The extract was washed with water, dried over magnesium sulfate, filtered and concentrated. The concentrate was flash chromatographed on silica gel with ethyl acetate.

Example 34D tert-butyl 2-(5-(4-carbamoyl-1H-benzimidazol-2-yl)thiophen-2-yl)pyrrolidine-1-carboxylate To a solution of EXAMPLE 34C (2.4 g) in pyridine (100 mL) and DMF (100 mL) was added CDI (1.6 g). The mixture was heated at 40° C. for 1 hour, treated with 2,3-diaminobenzamide dihydrochloride (1.8 g), stirred at ambient temperature overnight and concentrated. The concentrate was heated in acetic acid (50 mL) at 80° C. overnight and concentrated. The concentrate was flash chromatographed on silica gel with ethyl acetate.

Example 34E 2-(5-pyrrolidin-2-ylthien-2-yl)-1H-benzimidazole-4-carboxamide

A solution of EXAMPLE 34D (2.1 g) in dichloromethane (20 mL) and TFA (5 mL) was stirred at ambient temperature overnight and concentrated. The concentrate was purified by HPLC (Zorbax, C-18, Mobile phase A: 0.1% TFA in water; B: 0.1% TFA in acetonitrile; 0-100% gradient). $^1$H NMR (CD$_3$OD) δ 2.19-2.27 (m, 1H), 2.27-2.41 (m, 2H), 2.57-2.68 (m, 1H), 3.43-3.57 (m, 2H), 5.01 (dd, J=9.4, 6.9 Hz, 1H), 7.36 (t, J=7.7 Hz, 1H), 7.42 (d, J=4.6 Hz, 1H), 7.73 (dd, J=8.1, 1.1 Hz, 1H), 7.81 (d, J=4.0 Hz, 1H), 7.94 (dd, J=7.7, 0.9 Hz, 1H).

Example 35

2-(5-(1-methylpyrrolidin-2-yl)thien-2-yl)-1H-benzimidazole-4-carboxamide

This example was prepared as described in EXAMPLE 17, substituting EXAMPLE 34E for EXAMPLE 16D. $^1$H NMR (CD$_3$OD) δ 2.30 (m, 2H), 2.47 (m, 1H), 2.74 (m, 1H), 2.94 (s, 3H), 3.31-3.40 (m, 1H), 3.88 (m, 1H), 4.81 (m, 1H), 7.40 (t, J=7.7 Hz, 1H), 7.51 (d, J=3.7 Hz, 1H), 7.73 (d, J=7.6 Hz, 1H), 7.86 (d, J=4.0 Hz, 1H), 7.95 (d, J=7.6 Hz, 1H).

Example 36

2-(5-(1-isopropylpyrrolidin-2-yl)thien-2-yl)-1H-benzimidazole-4-carboxamide

This example was prepared as the trifluoroacetate salt as described in EXAMPLE 17, substituting EXAMPLE 34E for EXAMPLE 16D and acetone for formaldehyde. $^1$H NMR (CD$_3$OD) δ 1.40 (dd, J=12.2, 6.7 Hz, 6H), 2.20-2.35 (m, 2H), 2.34-2.46 (m, 1H), 2.67 (dd, J=12.0, 4.73 Hz, 1H), 3.39-3.52 (m, 1H), 3.58-3.64 (m, 1H), 3.64-3.73 (m, 1H), 5.00-5.08 (m, 1H), 7.40 (t, J=7.8 Hz, 1H), 7.51 (d, J=3.7 Hz, 1H), 7.76 (d, J=8.2 Hz, 1H), 7.85 (d, J=4.0 Hz, 1H), 7.95 (d, J=6.7 Hz, 1H).

Example 37

2-(5-(1-propylpyrrolidin-2-yl)thien-2-yl)-1H-benzimidazole-4-carboxamide

This example was prepared as the trifluoroacetate salt as described in EXAMPLE 17, substituting EXAMPLE 34E for EXAMPLE 16D and propionaldehyde for formaldehyde. $^1$H NMR (CD$_3$OD) δ 0.99 (t, J=7.4 Hz, 3H), 1.56-1.74 (m, 1H), 1.74-1.81 (m, 1H), 2.25-2.38 (m, 2H), 2.37-2.50 (m, 1H), 2.64-2.76 (m, 1H), 3.02-3.07 (m, 1H), 3.18-3.28 (m, 1H), 3.32-3.41 (m, 1H), 3.80-3.90 (m, 1H), 4.78-4.89 (m, 1H), 7.42 (t, J=7.8 Hz, 1H), 7.51 (d, J=3.7 Hz, 1H), 7.75 (d, J=7.1 Hz, 1H), 7.86 (d, J=3.7 Hz, 1H), 7.96 (d, J=6.7 Hz, 1H).

Example 38

2-(5-(1-(cyclopropylmethyl)pyrrolidin-2-yl)thien-2-yl)-1H-benzimidazole-4-carboxamide This example was prepared as the trifluoroacetate salt as described in EXAMPLE 17, substituting EXAMPLE 34E for EXAMPLE 16D and cyclopropanecarbaldehyde for formaldehyde. $^1$H NMR (CD$_3$OD) δ 0.30-0.33 (m, 1H), 0.40-0.44 (m, 1H), 0.63-0.81 (m, 2H), 0.98-1.18 (m, 1H), 2.26-2.39 (m, 2H), 2.39-2.51 (m, 1H), 2.61-2.80 (m, 1H), 3.01-3.11 (m, 1H), 3.11-3.21 (m, 1H), 3.38-3.53 (m, 1H), 3.92-4.07 (m, 1H), 4.80-4.90 (m, 1H), 7.40 (t, J=7.8 Hz, 1H), 7.49 (d, J=4.0 Hz, 1H), 7.74 (d, J=7.9 Hz, 1H), 7.85 (d, J=3.7 Hz, 1H), 7.94 (d, J=7.6 Hz, 1H).

Example 39

2-(5-(1-isobutylpyrrolidin-2-yl)thien-2-yl)-1H-benzimidazole-4-carboxamide

This example was prepared as the trifluoroacetate salt as described in EXAMPLE 17, substituting EXAMPLE 34E for EXAMPLE 16D and 2-methylpropionaldehyde for formaldehyde. $^1$H NMR (CD$_3$OD) δ 1.00 (dd, J=13.7, 6.7 Hz, 6H), 2.01-2.15 (m, 1H), 2.27-2.39 (m, 2H), 2.39-2.55 (m, 1H), 2.59-2.76 (m, 1H), 3.00-3.12 (m, 2H), 3.32-3.41 (m, 1H), 3.90-4.12 (m, 1H), 4.80-4.92 (m, 1H), 7.40 (t, J=7.8 Hz, 1H), 7.52 (d, J=3.7 Hz, 1H), 7.74 (d, J=8.0 Hz, 1H), 7.86 (d, J=4.0 Hz, 1H), 7.95 (d, J=6.7 Hz, 1H).

Example 40

2-(5-(1-cyclobutylpyrrolidin-2-yl)thien-2-yl)-1H-benzimidazole-4-carboxamide This example was prepared as the trifluoroacetate salt as described in EXAMPLE 17, substituting EXAMPLE 34E for EXAMPLE 16D and cyclobutanone for formaldehyde. $^1$H NMR (CD$_3$OD) δ 1.75-1.90 (m, 2H), 1.95-2.04 (m, 1H), 2.10-2.23 (m, 1H), 2.23-2.35 (m, 4H), 2.40-2.45 (m, 1H), 2.63-2.76 (m, 1H), 3.25-3.36 (m, 2H), 3.70-3.75 (m, 1H), 3.93-4.05 (m, 1H), 7.40 (t, J=7.8 Hz, 1H), 7.47 (d, J=4.0 Hz, 1H), 7.74 (d, J=8.0 Hz, 1H), 7.82 (d, J=3.7 Hz, 1H), 7.95 (d, J=7.7 Hz, 1H).

Example 41

2-(5-(1-cyclopentylpyrrolidin-2-yl)thien-2-yl)-1H-benzimidazole-4-carboxamide This example was prepared as the trifluoroacetate salt as described in EXAMPLE 17, substituting EXAMPLE 34E for EXAMPLE 16D and cyclopentanone for formaldehyde. $^1$H NMR (CD$_3$OD) δ 1.60-1.69 (m, 2H), 1.72-1.91 (m, 3H), 1.97-2.13 (m, 1H), 2.13-2.25 (m, 1H), 2.25-2.36 (m, 2H), 2.35-2.48 (m, 2H), 2.60-2.74 (m, 1H), 3.38-3.56 (m, 1H), 3.66-3.89 (m, 2H), 4.94-5.06 (m, 1H), 7.39 (t, J=7.9 Hz, 1H), 7.50 (d, J=4.0 Hz, 1H), 7.74 (d, J=7.1 Hz, 1H), 7.84 (d, J=3.99 Hz, 1H), 7.95 (d, J=7.7 Hz, 1H).

Example 42

2-(5-(1-cyclohexylpyrrolidin-2-yl)thien-2-yl)-1H-benzimidazole-4-carboxamide This example was prepared as the trifluoroacetate salt as described in EXAMPLE 17, substituting EXAMPLE 34E for EXAMPLE 16D and cyclohexanone for formaldehyde. $^1$H NMR (CD$_3$OD) δ 1.17-1.26 (m, 1H), 1.30-1.40 (m, 2H), 1.40-1.60 (m, 3H), 1.69-1.75 (m, 1H), 1.85-1.93 (m, 1H), 1.93-2.01 (m, 1H), 2.02-2.05 (m, 1H), 2.13-2.24 (m, 1H), 2.25-2.32 (m, 1H), 2.38-2.48 (m, 1H), 2.60-2.72 (m, 1H), 3.20-3.39 (m, 1H), 3.50-3.56 (m, 1H), 3.60-3.68 (m, 1H), 5.10-5.18 (m, 1H), 7.40 (t, J=7.8 Hz, 1H), 7.50 (d, J=3.7 Hz, 1H), 7.74 (d, J=8.0 Hz, 1H), 7.85 (d, J=3.7 Hz, 1H), 7.95 (d, J=7.4 Hz, 1H).

Example 43

2-(6-pyrrolidin-2-ylpyridin-3-yl)-1H-benzimidazole-4-carboxamide

To a mixture of 6-(1-(tert-butoxycarbonyl)pyrrolidin-2-yl)nicotinic acid (3 g, 10.6 mmol) in pyridine (10 mL) and N,N-dimethylformamide (50 mL) at ambient temperature was added 1,1'-carbonyldiimidazole (2.2 g, 16 mmol). The mixture was heated at 40° C. for 1 hour, treated with 2,3-diaminobenzamide dihydrochloride (2.4 g, 10.6 mmol), stirred at ambient temperature, for 16 hours and concentrated. The residue was heated in acetic acid (100 mL) at 110° C. for 2 hours, cooled and concentrated. The residue was purified by flash chromatography on silica gel using ethyl acetate to provide the acyclic intermediate. This intermediate was dissolved in dichloromethane (100 mL) and trifluoroacetic acid (20 mL) and the mixture was stirred at room temperature for 16 hours and was concentrated. The residue was purified by HPLC (Zorbax C-8, 0.1% trifluoroacetic acid/acetonitrile/water) to provide the title compound. $^1$H NMR (methanol-d$_4$) δ 2.04-2.36 (m, 3H), 2.49-2.74 (m, 1H), 3.39-3.72 (m, 2H), 4.98 (t, J=7.63 Hz, 1H), 7.17-7.49 (m, 1H), 7.69 (d, J=8.14 Hz, 1H), 7.81 (d, J=8.14 Hz, 1H), 7.99 (d, J=7.46 Hz, 1H), 8.64 (dd, J=8.31, 2.20 Hz, 1H), 9.42 (s, 1H).

Example 44

2-[6-(1-isopropylpyrrolidin-2-yl)pyridin-3-yl]-1H-benzimidazole-4-carboxamide The title compound was prepared as the trifluoroacetic acid salt as described in EXAMPLE 6, substituting acetone for formaldehyde and EXAMPLE 43 for EXAMPLE 5. $^1$H NMR (methanol-d$_4$) δ 1.34 (dd, J=7.97, 6.61 Hz, 6H), 1.98-2.31 (m, 3H), 2.56-2.77 (m, 1H), 3.41-3.57 (m, 1H), 3.58-3.84 (m, 2H), 4.99-5.13 (m, 1H), 7.31-7.52 (m, 1H), 7.73 (d, J=7.46 Hz, 1H), 7.82 (d, J=7.12 Hz, 1H), 8.00 (d, J=7.46 Hz, 1H), 8.67 (dd, J=8.31, 2.20 Hz, 1H), 9.46 (d, J=2.37 Hz, 1H).

Example 45

2-[6-(1-isobutylpyrrolidin-2-yl),pyridin-3-yl]-1H-benzimidazole-4-carboxamide

The title compound was prepared as the trifluoroacetic acid salt as described in EXAMPLE 6, substituting isobutyraldehyde for formaldehyde and EXAMPLE 43 for EXAMPLE 5. $^1$H NMR (methanol-$d_4$) δ 0.97 (d, J=6.74 Hz, 3H), 1.10 (d, J=6.74 Hz, 3H), 1.86-2.39 (m, 3H), 2.50-2.82 (m, 1H), 3.12 (d, J=7.14 Hz, 2H), 3.24-3.52 (m, 2H), 3.88-4.10 (m, 1H), 4.66-4.96 (m, 1H), 7.20-7.54 (m, 1H), 7.70 (d, J=7.93 Hz, 1H), 7.81 (d, J=7.93 Hz, 1H), 8.00 (d, J=6.74 Hz, 1H), 8.68 (dd, J=8.13, 2.18 Hz, 1H), 9.48 (d, J=1.98 Hz, 1H).

Example 46

2-[6-(1-cyclobutylpyrrolidin-2-yl),pyridin-3-yl]-1H-benzimidazole-4-carboxamide

The title compound was prepared as the trifluoroacetic acid salt as described in EXAMPLE 6, substituting cyclobutanone for formaldehyde and EXAMPLE 43 for EXAMPLE 5. $^1$H NMR (methanol-$d_4$) δ 1.63-1.89 (m, 2H), 1.84-2.04 (m, 2H), 2.08-2.45 (m, 6H), 2.47-2.72 (m, 1H), 3.66-3.88 (m, 1H), 3.97 (t, J=8.53 Hz, 1H), 4.67-4.98 (m, 1H), 7.23-7.55 (m, 1H), 7.70 (d, J=8.33 Hz, 1H), 7.81 (d, J=7.14 Hz, 1H), 8.00 (d, J=6.74 Hz, 1H), 8.64 (dd, J=8.13, 2.18 Hz, 1H), 9.50 (d, J=2.38 Hz, 1H).

Example 47

2-[6-(1-cyclopentylpyrrolidin-2-yl),pyridin-3-yl]-1H-benzimidazole-4-carboxamide The title compound was prepared as the trifluoroacetic acid salt as described in EXAMPLE 6, substituting cyclopentanone for formaldehyde and EXAMPLE 43 for EXAMPLE 5. $^1$H NMR (methanol-$d_4$) δ 1.37-1.52 (m, 1H), 1.51-1.69 (m, 2H), 1.67-2.01 (m, 4H), 2.02-2.38 (m, 4H), 2.56-2.80 (m, 1H), 3.41-3.56 (m, 1H), 3.69-3.96 (m, 2H), 4.92-5.05 (m, 1H), 7.43 (t, J=7.73 Hz, 1H), 7.72 (d, J=7.93 Hz, 1H), 7.81 (d, J=7.14 Hz, 1H), 8.00 (d, J=7.54 Hz, 1H), 8.67 (dd, J=8.13, 2.18 Hz, 1H), 9.48 (d, J=1.98 Hz, 1H).

Example 48

2-[6-(1-cyclohexylpyrrolidin-2-yl),pyridin-3-yl]-1H-benzimidazole-4-carboxamide

The title compound was prepared as the trifluoroacetic acid salt as described in EXAMPLE 6, substituting cyclohexanone for formaldehyde and EXAMPLE 43 for EXAMPLE 5. $^1$H NMR (methanol-$d_4$) δ 1.10-1.58 (m, 5H), 1.68 (d, J=12.29 Hz, 1H), 1.77-1.94 (m, 2H), 1.96-2.29 (m, 5H), 2.57-2.75 (m, 1H), 3.32-3.41 (m, 1H), 3.42-3.61 (m, 1H), 3.65-3.93 (m, 1H), 5.13 (dd, J=8.53, 6.54 Hz, 1H), 7.32-7.48 (m, 1H), 7.72 (d, J=8.33 Hz, 1H), 7.81 (d, J=7.14 Hz, 1H), 7.99 (d, J=7.54 Hz, 1H), 8.67 (dd, J=8.13, 2.18 Hz, 1H), 9.46 (d, J=1.59 Hz, 1H).

Example 49

2-[6-(1-tetrahydro-2H-pyran-4-ylpyrrolidin-2-yl),pyridin-3-yl]-1H-benzimidazole-4-carboxamide The title compound was prepared as the trifluoroacetic acid salt as described in EXAMPLE 6, substituting dihydro-2H-pyran-4(3H)-one for formaldehyde and EXAMPLE 43 for EXAMPLE 5. $^1$H NMR (methanol-$d_4$) δ 1.57-1.75 (m, 1H), 1.75-1.94 (m, 2H), 1.95-2.08 (m, 1H), 2.08-2.32 (m, 3H), 2.55-2.84 (m, 1H), 3.25-3.46 (m, 2H), 3.46-3.77 (m, 2H), 3.72-4.14 (m, 3H), 5.15 (dd, J=8.65, 6.27 Hz, 1H), 7.13-7.59 (m, 1H), 7.72 (d, J=7.80 Hz, 1H), 7.81 (d, J=7.12 Hz, 1H), 7.99 (d, J=6.44 Hz, 1H), 8.68 (dd, J=8.31, 2.20 Hz, 1H), 9.47 (d, J=1.36 Hz, 1H).

Example 50

2-[6-(1,3-oxazol-5-yl)pyridin-3-yl]-1H-benzimidazole-4-carboxamide

Example 50A 6-(oxazol-5-yl)nicotinic acid

To a suspension of methyl 6-formylnicotinate (60 mg, 0.363 mmol) in methanol (3 mL) was added sodium methoxide in methanol (0.5M, 2.91 mL, 1.45 mmol). Tosylmethyl isocyanide (85 mg, 0.436 mmol) was added to the reaction and the mixture was heated at reflux overnight. After cooling, the reaction mixture was concentrated. The residue was treated with 5% citric acid/50% brine (1:1) and extracted with ethyl acetate. The suspension was filtered, washed with water, and dried under vacuum to provide the title compound. MS (DCI/NH$_3$) m/z: 191.0 (M+1)$^+$.

Example 50B

N-(2-amino-3-carbamoylphenyl)-6-(oxazol-5-yl)nicotinamide

A solution of EXAMPLE 50A (60.0 mg, 0.316 mmol) in a mixture of pyridine (1.5 mL) and N,N-dimethylformamide (1.5 mL) was treated with 1,1'-carbonyldiimidazole (56.3 mg, 0.347 mmol) at 45° C. for 2 hours. After cooling, 2,3-diaminobenzamide (HCl salt) (70.7 mg, 0.316 mmol) was added and the mixture stirred at room temperature for 5 hours. After concentration, the residue was treated with 20% brine and ethyl acetate. The solid was filtered, washed with ethyl acetate and water, and dried under vacuum to provide the title compound. This material was used in the next step without further purification.

Example 50C

2-[6-(1,3-oxazol-5-yl)pyridin-3-yl]-1H-benzimidazole-4-carboxamide

A suspension of EXAMPLE 50B (24.0 mg, 0.074 mmol) in acetic acid (1 mL) was heated to 80° C. for 3 hours and cooled. The solution was concentrated and purified by HPLC (Zorbax, C-18, 250×2.54 column, Mobile phase A: 0.1% trifluoroacetic acid in H$_2$O; B: 0.1% trifluoroacetic acid in CH$_3$CN; 0-100% gradient) to provide the title compound as the trifluoroacetic acid salt. MS (DCI/NH$_3$) m/z: 306.2 (M+H)$^+$. $^1$H NMR (dimethylsulfoxide-$d_6$/D$_2$O) δ 7.45 (t, J=7.78 Hz, 1H), 7.84 (d, J=8.24 Hz, 1H), 7.93 (d, J=7.63 Hz, 1H), 7.96 (s, 1H), 8.01 (d, J=8.24 Hz, 1H), 8.60 (s, 1H), 8.71 (dd, J=8.39, 2.29 Hz, 1H), 9.44 (d, J=1.53 Hz, 1H).

Example 51

2-[5-(1,3,4-oxadiazol-2-yl)pyridin-2-yl]-1H-benzimidazole-4-carboxamide

Example 51A methyl 6-(2-amino-3-carbamoylphenylcarbamoyl)nicotinate

A solution of 5-(methoxycarbonyl)picolinic acid (3.33 g, 18.4 mmol) in a mixture of pyridine (20 mL) and N,N-dimethylformamide (35 mL) was treated with 1,1'-carbonyldiimidazole (3.28 g, 20.2 mmol) at 45° C. for 2 hours. After cooling, 2,3-diaminobenzamide (HCl salt) (4.12 g, 18.4 mmol) was added and the mixture stirred at room temperature overnight. The mixture was concentrated and the residue used in the next step without further purification.

Example 51B methyl 6-(4-carbamoyl-1H-benzo[d]imidazol-2-yl)nicotinate

The crude product from EXAMPLE 51A in acetic acid (40 ml) was heated to 90° C. for 1.5 hours. After cooling, the suspension was filtered. The filter cake was washed with acetic acid, and stirred in saturated NaHCO₃ for 30 minutes. The solid was filtered, washed with water and ether, and dried under vacuum to provide the title compound as an off-white solid. MS (DCI/NH₃) m/z: 297.1 (M+H)⁺.

Example 51C 6-(4-carbamoyl-1H-benzo[d]imidazol-2-yl)nicotinic acid

To a suspension of EXAMPLE 51B (2.00 g, 6.75 mmol) in tetrahydrofuran (36 ml) and methanol (12 mL) was added an emulsion of lithium hydroxide (0.850 g, 20.3 mmol) in water (8 mL) at room temperature. After 4 hours, most of the solvent was evaporated. The residue was dissolved in water and acidified with 5% citric acid until pH 5. The precipitate was filtered, washed with water and dried under vacuum to provide the title compound. MS (DCI/NH₃) m/z: 283.1 (M+H)⁺.

Example 51D 2-(5-(hydrazinecarbonyl)pyridin-2-yl)-1H-benzo[d]imidazole-4-carboxamide To a suspension of EXAMPLE 51C (1.40 g, 4.96 mmol) and TFFH (fluoro-N,N,N',N'-tetramethylformamidinium hexafluorophosphate, 1.57 g, 5.95 mmol) in N,N-dimethylformamide (18 mL) at 0° C. was added triethylamine (1.38 mL, 9.92 mmol) and hydrazine (0.311 mL, 9.92 mmol). The mixture was stirred at room temperature overnight. Water (60 mL) was added to the suspension and the solid was filtered, washed with water and ether and dried under vacuum to provide the title compound. MS (DCI/NH₃) m/z: 297.1 (M+H)+.

Example 51E

2-[5-(1,3,4-oxadiazol-2-yl)pyridin-2-yl]-1H-benzimidazole-4-carboxamide

A mixture of EXAMPLE 51D (70.0 mg, 0.236 mmol) and trimethyl orthoformate (1.50 mL, 13.6 mmol) in dimethylsulfoxide (0.5 mL) was heated at 150° C. for 30 minutes in a microwave reactor (CEM Explorer). After concentration the residue was purified by supercritical fluid chromatography (SFC) using a Princeton SFC pyridine 60 Å 5 μm (21.2 mm×150 mm) column and a gradient of 10-50% methanol (A) and carbon dioxide (B), at a flow rate of 40 mL/min. to provide the title compound. MS (APCI) m/z: 307.1 (M+H)⁺. ¹H NMR (dimethylsulfoxide-d₆) δ 7.38 (t, J=7.83 Hz, 1H), 7.73-7.82 (m, 2H), 7.91 (d, J=7.06 Hz, 1H), 8.55-8.70 (m, 2H), 9.31 (s, 1H, brd), 9.36 (d, J=1.84 Hz, 1H), 9.49 (s, 1H).

Example 52

2-{5-[5-(trifluoromethyl)-1,3,4-oxadiazol-2-yl]pyridin-2-yl}-1H-benzimidazole-4-carboxamide To a suspension of EXAMPLE 51D (70 mg, 0.236 mmol) in N,N-dimethylformamide (6 mL) was added trifluoroacetic acid (0.018 mL, 0.236 mmol) and 2-chloro-1,3-dimethylimidazolinium chloride (84 mg, 0.496 mmol). After 15 minutes, triethylamine (0.165 mL, 1.18 mmol) was added dropwise and the reaction stirred overnight. Water was added to the suspension and the solid was filtered, washed with water and ether and concentrated. The crude product was purified by HPLC (Zorbax, C-18, 250×2.54 column, Mobile phase A: 0.1% trifluoroacetic acid in H₂O; B: 0.1% trifluoroacetic acid in CH₃ CN; 0-100% gradient) to provide the title compound as the trifluoroacetic acid salt. MS (DCI/NH₃) m/z: 375.1 (M+H)⁺. ¹H NMR (dimethylsulfoxide-d₆) δ 7.43 (t, J=7.67 Hz, 1H), 7.80 (d, J=7.06 Hz, 1H), 7.84 (s, 1H), 7.94 (d, J=8.29 Hz, 1H), 8.63-8.74 (m, 2H), 9.15 (s, 1H, brd), 9.41 (s, 1H).

Example 53

2-[5-(5-methyl-1,3,4-oxadiazol-2-yl)pyridin-2-yl]-1H-benzimidazole-4-carboxamide To a suspension of EXAMPLE 51D (70 mg, 0.236 mmol) in N,N-dimethylformamide (6 mL) was added acetic acid (0.014 mL, 0.236 mmol) and 2-chloro-1,3-dimethylimidazolinium chloride (84 mg, 0.496 mmol). After 15 minutes, triethylamine (0.165 mL, 1.181 mmol) was added dropwise. The reaction was stirred for 5 hours. Water was added to the suspension and the solid was filtered. The filtrate was concentrated and purified by HPLC (Zorbax, C-18, 250×2.54 column, Mobile phase A: 0.1% trifluoroacetic acid in H₂O; B: 0.1% trifluoroacetic acid in CH₃ CN; 0-100% gradient) to provide the title compound as trifluoroacetic acid salt. MS (DCI/NH₃) m/z: 321.1 (M+H)⁺. ¹H NMR (dimethylsulfoxide-d₆) δ 2.34 (s, 3H), 7.43 (t, J=7.82 Hz, 1H), 7.81 (d, J=7.36 Hz, 1H), 7.85 (s, 1H), 7.94 (d, J=7.36 Hz, 1H), 8.50 (d, J=8.29 Hz, 1H), 8.66 (d, J=8.29 Hz, 1H), 9.13 (s, 1H, brd), 9.24 (s, 1H), 12.34 (s, 1H).

The foregoing is meant to illustrate the invention but not to limit it. Variations and changes obvious to one skilled in the art are intended to be within the scope of the invention as defined in the appended claims.

We claim:
1. A compound of Formula I

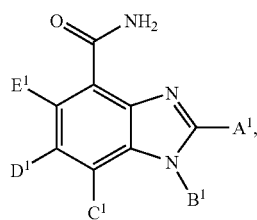

or a salt thereof, wherein
A$^1$ is heteroaryl which is substituted with A$^2$ and unfused;
A$^2$ is

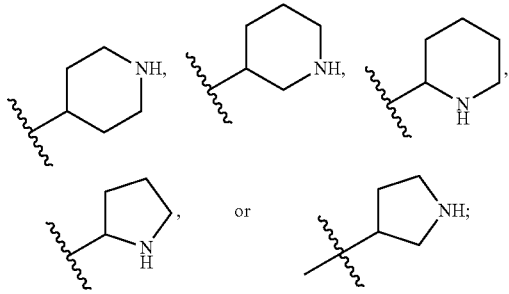

B$^1$ is hydrogen or R$^3$;
R$^3$ is alkyl;
C$^1$, D$^1$, E$^1$ are each independently hydrogen, NO$_2$, CN, R$^5$, OR$^5$, CO(O)R$^5$, C(O)NH$_2$, C(O)NHR$^5$, C(O)N(R$^5$)$_2$, NH$_2$, NHR$^5$, N(R$^5$)$_2$, OH F, Cl, Br or I;
R$^5$ is alkyl, alkenyl or alkynyl; each of which is unsubstituted or substituted with one or two substituents independently selected from R$^6$, NH$_2$, NHR$^6$, N(R$^6$)$_2$, C(O)NH$_2$, C(O)NHR$^6$, C(O)N(R$^6$)$_2$, OH, F, Cl, Br and I;
R$^6$ is alkyl or cycloalkyl;
wherein each foregoing cyclic moiety is independently unsubstituted or substituted with one or two or three or four or five substituents independently selected from R$^7$, OR$^7$, SR$^7$, S(O)R$^7$, SO$_2$R$^7$, C(O)R$^7$, CO(O)R$^7$, OC(O)R$^7$, OC(O)OR$^7$, NO$_2$, NH$_2$, NHR$^7$, N(R$^7$)$_2$, CH$_2$R$^7$, C(O)NH$_2$, C(O)NHR$^7$, C(O)N(R$^7$)$_2$, C(O)NHOH, C(O)NHOR$^7$, C(O)NHSO$_2$R$^7$, C(O)NR$^7$SO$_2$R$^7$, SO$_2$NH$_2$, SO$_2$NHR$^7$, SO$_2$N(R$^7$)$_2$, CF$_3$, CF$_2$CF$_3$, C(O)H, C(O)OH, C(N)NH$_2$, C(N)NHR$^7$, C(N)N(R$^7$)$_2$, CNOH, CNOCH$_3$, OH, (O), N$_3$, CF$_3$, CF$_2$CF$_3$, OCF$_3$, OCF$_2$CF$_3$, F, Cl, Br and I;
R$^7$ is R$^8$, R$^9$, R$^{10}$ or R$^{11}$;
R$^8$ is phenyl each of which is unfused or fused with benzene, heteroarene or R$^{8A}$; R$^{8A}$ is cycloalkane, cycloalkene, heterocycloalkane or heterocycloalkene;
R$^9$ is heteroaryl which is unfused or fused with benzene, heteroarene or R$^{9A}$; R$^{9A}$ is cycloalkane, cycloalkene, heterocycloalkane or heterocycloalkene;
R$^{10}$ is cycloalkyl, cycloalkenyl, heterocycloalkyl or heterocycloalkenyl, each of which is unfused or fused with benzene, heteroarene or R$^{10A}$; R$^{10A}$ is cycloalkane, cycloalkene, heterocycloalkane or heterocycloalkene;
R$^{11}$ is alkyl, alkenyl, or alkenyl, each of which is unsubstituted or substituted with one, two, three, four or five substituents independently selected from R$^{12}$, OR$^{12}$, SR$^{12}$, S(O)R$^{12}$, SO$_2$R$^{12}$, NH$_2$, NHR$^{12}$, N(R$^{12}$)$_2$, C(O)R$^{12}$, C(O)NH$_2$, C(O)NHR$^{12}$, C(O)N(R$^{12}$)$_2$, NHC(O)R$^{12}$, NR$^{12}$C(O)R$^{12}$, NHSO$_2$R$^{12}$, NR$^{12}$SO$_2$R$^{12}$, NHC(O)OR$^{12}$, NR$^{12}$C(O)OR$^{12}$, SO$_2$NH$_2$, SO$_2$NHR$^{12}$, SO$_2$N(R$^{12}$)$_2$, NHC(O)NH$_2$, NHC(O)R$^{12}$ NHC(O)N(R$^{12}$)$_2$, NR$^{12}$C(O)N(R$^{12}$)$_2$, OH, (O), C(O)OH, CN, CF$_3$, OCF$_3$, CF$_2$CF$_3$, F, Cl, Br and I;
R$^{12}$ is R$^{13}$, R$^{14}$, R$^{15}$ or R$^{16}$;
R$^{13}$ is phenyl which is unfused or fused with benzene, heteroarene or R$^{13A}$; R$^{13A}$ is cycloalkane, cycloalkene, heterocycloalkane or heterocycloalkene;
R$^{14}$ is heteroaryl which is unfused or fused with benzene, heteroarene or R$^{14A}$; R$^{14A}$ is cycloalkane, cycloalkene, heterocycloalkane or heterocycloalkene;
R$^{15}$ is cycloalkyl, cycloalkenyl, heterocycloalkyl or heterocycloalkenyl, each of which is unfused or fused with benzene, heteroarene or R$^{15A}$; R$^{15A}$ is cycloalkane, cycloalkene, heterocycloalkane or heterocycloalkene;
R$^{16}$ is alkyl, alkenyl or alkenyl, each of which is unsubstituted or substituted with R$^{17}$; and
R$^{17}$ is phenyl, heteroaryl, cycloalkyl, cycloalkenyl or heterocycloalkyl.

2. A compound of claim 1, wherein C$^1$, D$^1$, and E$^1$ are hydrogen.
3. A compound of claim 2, wherein B$^1$ is hydrogen.
4. A compound of claim 3, wherein A$^1$ is selected from the group consisting of

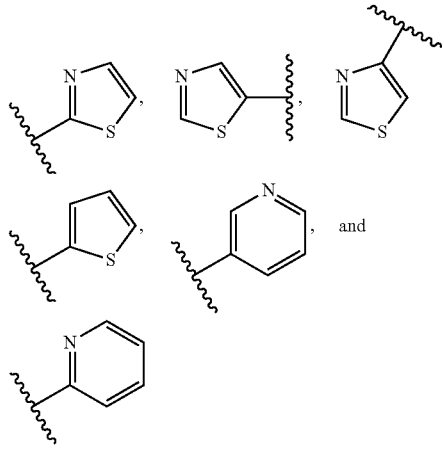

wherein each A$^1$ is substituted with A$^2$.
5. A compound of claim 4, wherein A$^2$ is unsubstituted or substituted with R$^7$ or CF$_3$.
6. A compound of claim 4, wherein A$^2$ is unsubstituted or substituted with R$^{10}$, R$^{11}$ or CF$_3$.
7. A compound of claim 4, wherein A$^2$ is unsubstituted or substituted with cycloalkyl, heterocycloalkyl, alkyl, or CF$_3$.
8. A compound of claim 4, wherein A$^2$ is unsubstituted or substituted with cycloalkyl, heterocycloalkyl, alkyl, or CF$_3$—; wherein the alkyl is unsubstituted or substituted with R$^{12}$; R$^{12}$ is R$^{14}$ or R$^{15}$; R$^{14}$ is heteroaryl which is unfused; and R$^{15}$ is cycloalkyl, which is unfused.
9. A compound of claim 8 which is
2-(2-piperidin-4-yl-1,3-thiazol-4-yl)-1H-1-benzimidazole-4-carboxamide, 2-(2-(1-methylpiperidin-4-yl)-1,3-thiazol-4-yl)-1H-benzimidazole-4-carboxamide,
2-(2-(1-isopropylpiperidin-4-yl)-1,3-thiazol-4-yl)-1H-benzimidazole-4-carboxamide,
2-(2-(1-propylpiperidin-4-yl)-1,3-thiazol-4-yl)-1H-benzimidazole-4-carboxamide,
2-(2-(1-cyclobutylpiperidin-4-yl)-1,3-thiazol-4-yl)-1H-benzimidazole-4-carboxamide,
2-(5-((2R)-pyrrolidin-2-yl)thien-2-yl)-1H-benzimidazole-4-carboxamide,
2-(5-((2R)-1-methylpyrrolidin-2-yl)thien-2-yl)-1H-benzimidazole-4-carboxamide,
2-(5-((2R)-1-isopropylpyrrolidin-2-yl)thien-2-yl)-1H-benzimidazole-4-carboxamide,
2-(5-((2R)-1-propylpyrrolidin-2-yl)thien-2-yl)-1H-benzimidazole-4-carboxamide,
2-(5-((2R)-(cyclopropylmethyl)pyrrolidin-2-yl)thien-2-yl)-1H-benzimidazole-4-carboxamide,
2-(5-((2R)-1-cyclobutylpyrrolidin-2-yl)thien-2-yl)-1H-benzimidazole-4-carboxamide,
2-(5-((2R)-1-cyclopentylpyrrolidin-2-yl)thien-2-yl)-1H-benzimidazole-4-carboxamide,
2-(5-((2R)-1-cyclohexylpyrrolidin-2-yl)thien-2-yl)-1H-benzimidazole-4-carboxamide,
2-(5-((2R)-1-tetrahydro-2H-pyran-4-ylpyrrolidin-2-yl)thien-2-yl)-1H-benzimidazole-4-carboxamide,
2-(5-((2R)-1-(pyridin-2-ylmethyl)pyrrolidin-2-yl)thien-2-yl)-1H-benzimidazole-4-carboxamide,
2-(5-((2R)-1-(pyridin-4-ylmethyl)pyrrolidin-2-yl)thien-2-yl)-1H-benzimidazole-4-carboxamide,
2-(5-((2R)-1-isobutylpyrrolidin-2-yl)thien-2-yl)-1H-benzimidazole-4-carboxamide,
2-(5-piperidin-2-ylthien-2-yl)-1H-benzimidazole-4-carboxamide,
2-(5-(1-methylpiperidin-2-yl)thien-2-yl)-1H-benzimidazole-4-carboxamide,
2-(5-(1-propylpiperidin-2-yl)thien-2-yl)-1H-benzimidazole-4-carboxamide,
2-(5-(1-(cyclopropylmethyl)piperidin-2-yl)thien-2-yl)-1H-benzimidazole-4-carboxamide,
2-(5-(1-cyclobutylpiperidin-2-yl)thien-2-yl)-1H-benzimidazole-4-carboxamide,
2-(5-(1-isobutylpiperidin-2-yl)thien-2-yl)-1H-benzimidazole-4-carboxamide,
2-(5-pyrrolidin-2-ylthien-2-yl)-1H-benzimidazole-4-carboxamide,
2-(5-(1-methylpyrrolidin-2-yl)thien-2-yl)-1H-benzimidazole-4-carboxamide,
2-(5-(1-isopropylpyrrolidin-2-yl)thien-2-yl)-1H-benzimidazole-4-carboxamide,
2-(5-(1-propylpyrrolidin-2-yl)thien-2-yl)-1H-benzimidazole-4-carboxamide,
2-(5-(1-(cyclopropylmethyl)pyrrolidin-2-yl)thien-2-yl)-1H-benzimidazole-4-carboxamide,
2-(5-(1-isobutylpyrrolidin-2-yl)thien-2-yl)-1H-benzimidazole-4-carboxamide,
2-(5-(1-cyclobutylpyrrolidin-2-yl)thien-2-yl)-1H-benzimidazole-4-carboxamide,
2-(5-(1-cyclopentylpyrrolidin-2-yl)thien-2-yl)-1H-benzimidazole-4-carboxamide,
2-(5-(1-cyclohexylpyrrolidin-2-yl)thien-2-yl)-1H-benzimidazole-4-carboxamide,
2-(6-pyrrolidin-2-ylpyridin-3-yl)-1H-benzimidazole-4-carboxamide;
2-[6-(1-isopropylpyrrolidin-2-yl)pyridin-3-yl]-1H-benzimidazole-4-carboxamide;
2-[6-(1-isobutylpyrrolidin-2-yl)pyridin-3-yl]-1H-benzimidazole-4-carboxamide;
2-[6-(1-cyclobutylpyrrolidin-2-yl)pyridin-3-yl]-1H-benzimidazole-4-carboxamide;
2-[6-(1-cyclopentylpyrrolidin-2-yl)pyridin-3-yl]-1H-benzimidazole-4-carboxamide;
2-[6-(1-cyclohexylpyrrolidin-2-yl)pyridin-3-yl]-1H-benzimidazole-4-carboxamide; or
2-[6-(1-tetrahydro-2H-pyran-4-ylpyrrolidin-2-yl)pyridin-3-yl]-1H-benzimidazole-4-carboxamide;
or a pharmaceutically acceptable salt thereof.

10. A pharmaceutical composition comprising a compound of claim 1 and pharmaceutically acceptable excipient.

* * * * *

UNITED STATES PATENT AND TRADEMARK OFFICE
CERTIFICATE OF CORRECTION

PATENT NO. : 8,067,613 B2  
APPLICATION NO. : 12/173213  
DATED : November 29, 2011  
INVENTOR(S) : Gandhi et al.

Page 1 of 1

It is certified that error appears in the above-identified patent and that said Letters Patent is hereby corrected as shown below:

On the Title Page, Item (54) and Col. 1, line 1-2, title: "(ADP RIBOSE)" to read as
-- (ADP-RIBOSE) --

Column 53, line 40, claim 1: "OH F," to read as -- OH, F, --

Column 54, line 08, claim 1: "NHC(O)$R^{12}$ NHC(O)N($R^{12}$)$_2$," to read as
-- NHC(O)$R^{12}$NHC(O)N($R^{12}$)$_2$, --

Column 54, line 66, claim 9: "-1H-1-" to read as -- -1H- --

Signed and Sealed this
Sixteenth Day of October, 2012

David J. Kappos
*Director of the United States Patent and Trademark Office*